US010188756B2

(12) United States Patent
Hooker et al.

(10) Patent No.: US 10,188,756 B2
(45) Date of Patent: Jan. 29, 2019

(54) IMAGING HISTONE DEACETYLASES WITH A RADIOTRACER USING POSITRON EMISSION TOMOGRAPHY

(71) Applicant: THE GENERAL HOSPITAL CORPORATION, Boston, MA (US)

(72) Inventors: Jacob M. Hooker, Charlestown, MA (US); Changning Wang, Acton, MA (US); Frederick Albert Schroeder, Baltimore, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/030,214

(22) PCT Filed: Oct. 17, 2014

(86) PCT No.: PCT/US2014/061179
§ 371 (c)(1),
(2) Date: Apr. 18, 2016

(87) PCT Pub. No.: WO2015/058106
PCT Pub. Date: Apr. 23, 2015

(65) Prior Publication Data
US 2016/0271276 A1 Sep. 22, 2016

Related U.S. Application Data

(60) Provisional application No. 61/892,966, filed on Oct. 18, 2013.

(51) Int. Cl.
| | |
|---|---|
| *A61K 51/04* | (2006.01) |
| *C07C 259/06* | (2006.01) |
| *C07C 259/08* | (2006.01) |
| *C07C 275/34* | (2006.01) |
| *C07C 311/16* | (2006.01) |
| *C07C 311/21* | (2006.01) |
| *C07D 235/08* | (2006.01) |
| *C07D 267/16* | (2006.01) |
| *C07D 209/08* | (2006.01) |
| *C07D 209/14* | (2006.01) |
| *C07D 281/12* | (2006.01) |

(52) U.S. Cl.
CPC ............ *A61K 51/04* (2013.01); *C07C 259/06* (2013.01); *C07C 259/08* (2013.01); *C07C 275/34* (2013.01); *C07C 311/16* (2013.01); *C07C 311/21* (2013.01); *C07D 209/08* (2013.01); *C07D 209/14* (2013.01); *C07D 235/08* (2013.01); *C07D 267/16* (2013.01); *C07D 281/12* (2013.01); *C07B 2200/05* (2013.01); *C07C 2601/14* (2017.05); *C07C 2602/10* (2017.05); *C07C 2603/74* (2017.05)

(58) Field of Classification Search
None
See application file for complete search history.

(56) References Cited

U.S. PATENT DOCUMENTS

| 8,476,255 B2 | 7/2013 | Rajagopal et al. |
| 2004/0106599 A1 | 6/2004 | Delorme et al. |
| 2008/0103391 A1 | 5/2008 | Dos Santos Varela |
| 2010/0249197 A1 | 9/2010 | Watkins et al. |
| 2010/0317739 A1 | 12/2010 | Brown et al. |
| 2011/0071109 A1 | 3/2011 | Wiest et al. |
| 2011/0212943 A1* | 9/2011 | Balasubramanian ........................ C07C 237/20 514/216 |
| 2011/0312956 A1 | 12/2011 | Jackson et al. |

FOREIGN PATENT DOCUMENTS

WO  2010043953 A2  4/2010

OTHER PUBLICATIONS

Jacob M. Hooker et al., Histone Deactrylase Inhibitor MS-275 Exhibits Poor Brain Penetration: Pharmacokenitic Studies of [11C]MS-275 using Positron Emission Tomogrpahy, ACS Chem. Neuroscience, 2010, 1, 65-73. (Year: 2010).*
Acharya, et al., Rational Development of Histone Deacetylase Inhibitors as Anticancer Agents: A Review, Mol. Pharmacol., 2005, 68:917-932.
Alexoff, et al., Plasma Input Function Determination for PET Using a Commercial Laboratory Robot, Nuclear Medicine and Biology, 1995, 22(7):893-904.
Alexoff, et al., Reproducibility of 11C-Raclopride Binding in the Rat Brain Measured with the MicroPET R4: Effects of Scatter Correction and Tracer Specific Activity, J. Nucl. Med., 2003, 44:815-822.
Andersson, et al., Synthesis of 11C-Labelled Benzamide Compounds as Potential Tracers for Poly(ADP-ribose) Synthetase, Applied Radiation and Isotopes, 1994, 45(6):707-714.
Balasubramanian, Isoform-Specific Histone Deacetylase Inhibitors: The Next Step?, Cancer Letters, 2009, 280(2):211-221.

(Continued)

*Primary Examiner* — Michael G. Hartley
*Assistant Examiner* — Jagadishwar R Samala
(74) *Attorney, Agent, or Firm* — Quarles & Brady LLP

(57) ABSTRACT

Disclosed herein are histone deacetylase imaging agents for positron emission tomography and related imaging methods using the histone deacetylase imaging agents. The histone deacetylase imaging agents may be a compound of formula (I): wherein $R^1$ is a moiety including a positron emitter; $R^2$ represents hydrogen, or substituted or unsubstituted alkyl, or substituted or unsubstituted aryl, or substituted or unsubstituted heteroaryl; and n is an integer selected from 0 or 1. In one version of the compound of formula (I), $R^1$ is a moiety including an adamantyl group.

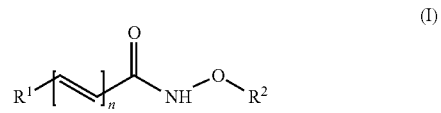

(I)

11 Claims, 14 Drawing Sheets

(56) References Cited

OTHER PUBLICATIONS

Barnes, Targeting the Epigenome in the Treatment of Asthma and Chronic Obstructive Pulmonary Disease, Proc. Am. Thorac. Soc., 2009, 6:693-696.
Berndsen, et al., Assays for Mechanistic Investigations of Protein/Histone Acetyltransferases, Methods, 2005, 36:321-331.
Bieliauskas, et al., Isoform-Selective Histone Deacetylase Inhibitors, Chem. Soc. Rev., 2008, 37(7):1402-1413.
Bowers, et al., The Total Synthesis and Biological Mode of Action of Largazole: A Potent Class I Histone Deacetylase (HDAC) Inhibitor, J. Am. Chem. Soc., 2008, 130(33):11219-11222.
Bush, et al., Targeting Histone Deacetylases for Heart Failure, Expert Opinion on Therapeutic Targets, 2009, 13(7):767-784.
Chuang, et al., Multiple Roles of HDAC Inhibition in Neurodegenerative Conditions, Trends Neurosci., 2009, 32(11):591-601.
Clark, et al., DNA Methylation: Bisulphite Modification and Analysis, Nature Protocols, 2006, 1(5):2353-2364.
Cosio, et al., Histone Acetylase and Deacetylase Activity in Alveolar Macrophages and Blood Mononocytes in Asthma, Am. J. Respir. Crit. Care. Med., 2004, 170:141-147.
Dai, et al., A Novel Series of Histone Deacetylase Inhibitors Incorporating Hetero Aromatic Ring Systems as Connection Units, Bioorganic & Medicinal Chemistry Letters, 2003, 13:3817-3820.
Finnin, et al., Structures of a Histone Deacetylase Homologue Bound to the TSA and SAHA Inhibitors, Nature, 1999, 401:188-193.
Fournel, et al., Sulfonamide Anilides, a Novel Class of Histone Deacetylase Inhibitors, Are Antiproliferative Against Human Tumors, Cancer Research, 2002, 62:4325-4330.
Fritzsche, et al., Class I Histone Deacetylases I, 2 and 3 are Highly Expressed in Renal Cell Cancer, BMC Cancer, 2008, 8:381, pp. 1-10.
Gallo, et al., Inhibition of Class I Histone Deacetylase with an Apicidin Derivative Prevents Cardiac Hypertrophy and Failure, Cardiovascular Research, 2008, 80:416-424.
Gatley, et al., Rapid Stereoselective Hydrolysis of (+)-Cocaine in Baboon Plasma Prevents Its Uptake in the Brain: Implications for Behavioral Studies, Journal of Neurochemistry, 1990, 54(2):720-733.
Glaser, et al., Gene Expression Profiling of Multiple Histone Deacetylase (HDAC) Inhibitors: Defining a Common Gene Set Produced by HDAC Inhibition in T24 and MDA Carcinoma Cell Lines, Molecular Cancer Therapeutics, 2003, 2:151-163.
Gopalan, et al., Discovery of Adamantane Based Highly Potent HDAC Inhibitors, Bioorganic & Medicinal Chemistry Letters, 2013, 23:2532-2537.
Graff, et al., Review Article—Epigenetic Dysregulation in Cognitive Disorders, European Journal of Neuroscience, 2009, 30:1-8.
Guan, et al., HDAC2 Negatively Regulates Memory Formation and Synaptic Plasticity, Nature, 2009, 459:55-60.
Halili, et al., Histone Deacetylase Inhibitors in Inflammatory Disease, Current Topics in Medicinal Chemistry, 2009, 9(3):309-319.
Harms, et al., Histone Deacetylase 2 Modulates p53 Transcriptional Activities Through Regulation of p53-DNA Binding Activity, Cancer Research, 2007, 67(7):3145-3152.
Holland, et al., Unconventional Nuclides for Radiopharmaceuticals, Molecular Imaging, 2010, 9(1):1-20.
Hong, et al., A Novel Domain in Histone Deacetylase 1 and 2 Mediates Repression of Cartilage-Specific Genes in Human Chondrocytes, FASEB J., 2009, 23:3539-3552.
Hooker, et al., A Simple, Rapid Method for the Preparation of [11C]formaldehyde, Angew. Chem. Int. Ed. Engl., 2008, 47(32):5989-5992.
Hooker, et al., One-Pot Direct Incorporation of [11C]—CO2 Into Carbamates, Angew. Chem. Int. Ed. Engl., 2009, 48(19):3482-3485.
Hooker, et al., Salvinorin A and Derivatives: Protection from Metabolism Does Not Prolong Short-Term, Whole-Brain Residence, Neuropharmacology, 2009, 57(4):386-391.
Hooker, et al., Histone Deacetylase Inhibitor MS-275 Exhibits Poor Brain Penetration: Pharmacokinetic Studies of [11C]MS-275 Using Positron Emission Tomography, ACS Chem. Neurosci., 2010, 1:65-73.
Hooker, Modular Strategies for PET Imaging Agents, Curr. Opin. Chem. Biol., 2010, 14(1):105.
Howard, et al., Plasma Protein Binding in Drug Discovery and Development, Combinatorial Chemistry & High Throughput Screening, 2010, 13:000-000, 18 pp.
Hu, et al., Identification of Novel Isoform-Selective Inhibitors within Class I Histone Deacetylases, Journal of Pharmacology and Experimental Therapeutics, 2003, 307(2):720-728.
Ishihama, et al., Expression of HDAC1 and CBP/p300 in Human Colorectal Carcinomas, J. Clin. Pathol., 2007, 60:1205-1210.
Ito, et al., Expression and Activity of Histone Deacetylases in Human Asthmatic Airways, Am. J. Respir. Crit. Care Med., 2002, 166:392-396.
Jin, et al., Expression Profile of Histone Deacetylases 1, 2 and 3 in Ovarian Cancer Tissues, J. Gynecol. Oncol., 2008, 19(3):185-190.
Johnstone, et al., Histone Deacetylase Inhibitors in Cancer Therapy: Is Transcription the Primary Target?, Cancer Cell, 2003, 4:13-18.
Kee, et al., Inhibition of Histone Deacetylation Blocks Cardiac Hypertrophy Induced by Angiotensin II Infusion and Aortic Banding, Circulation, 2006, 113:51-59.
Kee, et al., Activation of Histone Deacetylase 2 by Inducible Heat Shock Protein 70 in Cardiac Hypertrophy, Cir. Res., 2008, 103:1259-1269.
Khabele et al., Drug-Induced Inactivation or Gene Silencing of Class I Histone Deacetylases Suppresses Ovarian Cancer Cell Growth, Cancer Biology & Therapy, 2007, 6(5):795-801.
Kilgore, et al., Inhibitors of Class I Histone Deacetylases Reverse Contextual Memory Deficits in a Mouse Model of Alzheimer's Disease, Neuropsychopharmacology, 2010, 35(4):870-880.
Kim, et al., Histone Deacetylases Induce Angiogenesis by Negative Regulation of Tumor Suppressor Genes, Nature Medicine, 2001, 7(4):437-443.
Kouzarides, Chromatin Modifications and Their Function, Cell, 2007, 128:693-705.
Kuninger, et al., A Non-Isotopic In Vitro Assay for Histone Acetylation, J. Biotechnol., 2007, 131(3):253-260.
Lagger, et al., Essential Function of Histone Deacetylase 1 in Proliferation Control and CDK Inhibitor Repression, The EMBO Journal, 2002, 21(11):2672-2681.
Laruelle et al., Relationships Between Radiotracer Properties and Image Quality in Molecular Imaging of the Brain with Positron Emission Tomography, Molecular Imaging & Biology, 2003, 5(6):363-375.
Lin, et al., Anti-Rheumatic Activities of Histone Deacetylase (HDAC) Inhibitors In Vivo in Collagen-Induced Arthritis in Rodents, British Journal of Pharmacology, 2007, 150:862-872.
Logan, A Review of Graphical Methods for Tracer Studies and Strategies to Reduce Bias, Nuclear Medicine and Biology, 2003, 30:833-844.
Ma, et al., Histone Deacetylase Inhibitors, Current Status and Overview of Recent Clinical Trials, Drugs, 2009, 69(14):1911-1934.
Mai, et al., Histone Deacetylase Inhibitors and Neurodegenerative Disorders: Holding the Promise, Current Pharmaceutical Design, 2009, 15:3940-3957.
Meikle, et al., Complementary Molecular Imaging Technologies: High Resolution SPECT, PET and MRI, Drug Discovery Today: Technologies, 2006, 3(2):187-194.
Miller, P., et al., Synthesis of 11C, 18F, 15O, and 13N Radiolabels for Positron Emission Tomography, Angew. Chem. Int. Ed. Engl., 2008, 47(47):8998-9033.
Miller, T., et al., Histone Deacetylase Inhibitors, Journal of Medicinal Chemistry, 2003, 46(24):5097-5116.
Minucci, et al., Histone Deacetylase Inhibitors and the Promise of Epigenetic (and more) Treatments for Cancer, Nature Reviews Cancer, 2006, 6(1):38-51.
Mitsiades, et al., Transcriptional Signature of Histone Deacetylase Inhibition in Multiple Myeloma: Biological and Clinical Implications, PNAS, 2004, 101(2):540-545.

(56) References Cited

OTHER PUBLICATIONS

Montgomery, et al., Histone Deacetylases 1 and 2 Redundantly Regulate Cardiac Morphogenesis, Growth, and Contractility, Genes & Development, 2007, 21:1790-1802.
Montgomery, et al., Maintenance of Cardiac Energy Metabolism by Histone Deacetylase 3 in Mice, Journal of Clinical Investigation, 2008, 118(11):3588-3597.
Newkirk, et al., Discovery, Biological Activity, Synthesis and Potential Therapeutic Utility of Naturally Occurring Histone Deacetylase Inhibitors, Natural Product Reports, 2009, 26:1293-1320.
Reid, et al., Evaluation of 6-([18F]fluoroacetamido)-1-hexanoicanilide for PET Imaging of Histone Deacetylase in the Baboon Brain, Nucl. Med. Biol., 2009, 36(3):247-258.
Riss, et al., [11C]PR04.MZ, a Promising DAT Ligand for Low Concentration Imaging: Synthesis, Efficient 11C—O-methylation and Initial Small Animal PET Studies, Bioorganic & Medicinal Chemistry Letters, 2009, 19(15):4343-4345.
Saito, et al., A Synthetic Inhibitor of Histone Deacetylase, MS-27-275, with Marked In Vivo Antitumor Activity Against Human Tumors, Proc. Natl. Acad. Sci., 1999, 96:4592-4597.
Scott, Methods for the Incorporation of Carbon-11 to Generate Radiopharmaceuticals for PET Imaging, Angew. Chem. Int. Ed., 2009, 48:6001-6004.
Sharma, et al., Epigenetics in Cancer, Carcinogenesis, 2010, 31(1):27-36.
Somoza, et al., Structural Snapshots of Human HDAC8 Provide Insights Into the Class I Histone Deacetylases, Structure, 2004, 12:1325-1334.
Sorensen, et al., Immunoprecipitation of Methylated DNA, Methods in Molecular Biology, 2009, 567:249-262.
Stabin, et al., OLINDA/EXM: The Second-Generation Personal Computer Software for Internal Dose Assessment in Nuclear Medicine, J. Nucl. Med., 2005, 46:1023-1027.
Stimson, et al., Biomarkers for Predicting Clinical Responses to HDAC Inhibitors, Cancer Letters, 2009, 280(2):177-183.
Suzuki, M., et al., DNA Methylation Landscapes: Provocative Insights from Epigenomics, Nature Reviews Genetics, 2008, 9:465-476.
Suzuki, T., et al., Synthesis and Histone Deacetylase Inhibitory Activity of New Benzamide Derivatives, J. Med. Chem, 1999, 42:3001-3003.
Thiebaut, et al., Cellular Localization of the Multidrug-Resistance Gene Product P-glycoprotein in Normal Human Tissues, Proc. Natl. Acad. Sci., 1987, 84:7735-7738.
Trivedi, et al., Hdac2 Regulates the Cardiac Hypertrophic Response by Modulating Gsk3β Activity, Nature Medicine, 2007, 13(3):324-331.
Wang, C., et al., Visualizing Epigenetics: Current Advances and Advantages in HDAC PET Imaging Techniques, Neuroscience, 2014, 264:186-197.
Wang, D., et al., Toward Selective Histone Deacetylase Inhibitor Design: Homology Modeling, Docking Studies, and Molecular Dynamics Simulations of Human Class I Histone Deacetylases, Journal of Medicinal Chemistry, 2005, 48(22):6936-6947.
Wang, D., Computational Studies on the Histone Deacetylases and the Design of Selective Histone Deacetylase Inhibitors, Curr. Top. Med. Chem., 2009, 9(3):241-256.
Waterhouse, et al., Determination of Lipophilicity and Its Use as a Predictor of Blood-Brain Barrier Penetration of Molecular Imaging Agents, Molecular Imaging & Biology, 2003, 5(6):376-389.
Wegener, et al., A Fluorogenic Histone Deacetylase Assay Well Suited for High-Throughput Activity Screening, Chemistry & Biology, 2003, 10:61-68.
Wegener, et al., Identification of Novel Small-Molecule Histone Deacetylase Inhibitors by Medium-Throughput Screening Using a Fluorigenic Assay, Biochem J., 2008, 413:143-150.
Wilson, et al., Novel Radiotracers for Imaging the Serotonin Transporter by Positron Emission Tomography: Synthesis, Radiosynthesis, and In Vitro and Ex Vivo Evaluation of 11C-Labeled 2-(Phenylthio)araalkylamines, J. Med. Chem., 2000, 43:3103-3110.
Wong, et al., Predicting the Success of a Radiopharmaceutical for In Vivo Imaging of Central Nervous System Neuroreceptor Systems, Molecular Imaging & Biology, 2003, 5(6):350-362.
Yoshida, et al., Potent and Specific Inhibition of Mammalian Histone Deacetylase Both In Vivo and In Vitro by Trichostatin A, Journal of Biological Chemistry, 1990, 265(28):17174-17179.
Zhu, et al., Induction of HDAC2 Expression Upon Loss of APC in Colorectal Tumorigenesis, Cancer Cell, 2004, 5:455-463.
PCT International Search Report and Written Opinion, PCT/US2014/061179, dated Jan. 7, 2015.
Balasubramanian Gopalan et al., "Discovery of Adamantane Based Highly Potent HDAC Inhibitors", Biorganic & Medicinal Chemistry Letters, vol. 23, Mar. 14, 2013; pp. 2532-2537.

\* cited by examiner

IMAGING HISTONE DEACETYLASES WITH A RADIOTRACER USING POSITRON EMISSION TOMOGRAPHY

CROSS-REFERENCES TO RELATED APPLICATIONS

This application is a 371 application of PCT/US2014/061179 filed Oct. 17, 2014 which claims priority from U.S. Patent Application No. 61/892966 filed Oct. 18, 2013.

STATEMENT REGARDING FEDERALLY SPONSORED RESEARCH

This invention was made with government support under grant number R01DA030321 awarded by National Institutes of Health. The government has certain rights in the invention.

BACKGROUND OF THE INVENTION

1. Field of the Invention

The invention relates to histone deacetylase imaging agents for positron emission tomography.

2. Description of the Related Art

Millions of people in the United States and all over the world are affected by brain disorders, heart disease and cancers. Decades of research in both industry and academia have failed in many cases to develop highly effective treatments. Modulation of epigenetic processes may be a new therapeutic approach applicable across most human diseases. Investigation of epigenetic changes, DNA methylation and post-translational modification of histone proteins, in the brain has provided new insight into the mediators of diverse central nervous system (CNS) disorders. However, visualizing human brain function is a challenge since the human brain is inaccessible and difficult to assay directly. Non-invasive imaging techniques, such as magnetic resonance imaging (MRI) and positron emission tomography (PET), have been used in the clinical setting for imaging brain functions and disorders. Depending on the nature of the PET radiotracer or MRI sequence selected, these techniques can be used to probe structure, function, neurochemistry, or drug pharmacokinetics.

Numerous efforts have been made to develop noninvasive tools for imaging epigenetic modulators, for the detection and quantification of expression in vivo, which is critical to assess the efficacy of therapies targeting epigenetic mechanisms and to clarify the understanding of the mechanism of enzyme dysfunction in disease. Histone deacetylase is one of the most intensely investigated epigenetic enzymes, and recent studies have demonstrated that histone deacetylase enzymes are associated with numerous brain dysfunctions and disorders. To date, however, there are no validated techniques for the assessment of such enzymes in the human brain. PET is an excellent tool for the in vivo quantification of histone deacetylase biological processes and evaluates the pattern of histone deacetylase distribution in animals and human. A major advantage of PET technique is extraordinarily high sensitivity ($10^{-9}$ to $10^{-12}$ M), and more sensitive than MRI ($10^{-4}$ M). PET is also able to quantify the distribution of radiotracers in the brain in vivo and correlate in vitro measurement outcomes with invasive techniques such as autoradiography, immunohistochemistry and western immunoblotting. However, the lack of histone deacetylase PET imaging agents has hindered the use of PET to directly assess histone deacetylases in vivo.

Therefore, there exists a need for a radiotracer for imaging histone deacetylases using positron emission tomography.

SUMMARY OF THE INVENTION

To accelerate the application of this knowledge to human disease, we have developed translational neuroimaging methodology to both visualize and quantify the histone deacetylases. The development of a PET radiotracer for epigenetic status allows for the characterization of normal epigenetic status in vivo as a function of normal processes, and could be used as a powerful tool for early diagnosis of human diseases with abnormal epigenetic status (e.g., cancer, cognitive and psychiatric disorders, and heart and inflammatory diseases). A PET radiotracer can also be used to measure the effects of therapeutic drug treatment.

It is preferred if the radiotracers have fast on, slow off binding kinetics to visualize in a relevant time setting. As expected, a slow-on compound would likely not be appropriate for in vivo imaging. For example, the benzamide-based histone deacetylase (HDAC) inhibitors have been shown to exhibit slow-on kinetics in binding to histone deacetylases. Given radioisotope labeling with carbon-11 for PET imaging, longer targeting time would therefore be required to obtain sufficient detectable signal to visualize HDAC binding. In this specification, we report the synthesis and characterization of adamantane-based hydroxamic acids as histone deacetylase PET imaging agents with the properties required to target histone deacetylases in brain and peripheral organs in vivo.

The histone deacetylase PET imaging agents may be a compound of formula (I):

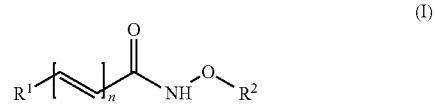

wherein $R^1$ is a moiety including a contrast agent; $R^2$ represents hydrogen, substituted or unsubstituted alkyl, substituted or unsubstituted aryl, substituted or unsubstituted heteroaryl, or substituted or unsubstituted heterocyclic; and n is an integer selected from 0 or 1. In one version of the compound of formula (I), $R^1$ is a moiety including an adamantyl group, $R^2$ represents hydrogen, and n is 1.

It is an advantage of the invention to enable non-invasive and repetitive in vivo imaging of expression and activity of histone deacetylases in the brain and different organs and tissues (including cancer).

It is another advantage of the invention to help to understand the mechanisms of histone deacetylases involvement in normal physiology and in the mechanisms of different diseases.

It is yet another advantage of the invention to provide a predictive tool for individual drug response to histone deacetylase inhibitors.

It is still another advantage of the invention to accelerate the development of new histone deacetylase inhibitors.

It is yet another advantage of the invention to provide a PET radiotracer for imaging histone deacetylases wherein the radiotracer can cross the blood-brain barrier.

It is still another advantage of the invention to provide a PET radiotracer that has high brain uptake and high specific binding.

These and other features, aspects, and advantages of the present invention will become better understood upon consideration of the following detailed description, drawings, and appended claims.

BRIEF DESCRIPTION OF THE DRAWINGS

FIG. 9 also shows the time-activity curves in the baboon organs with a pretreatment with the unlabeled hydroxyacrylamide of FIG. 3.

DETAILED DESCRIPTION OF THE INVENTION

Figure 1:
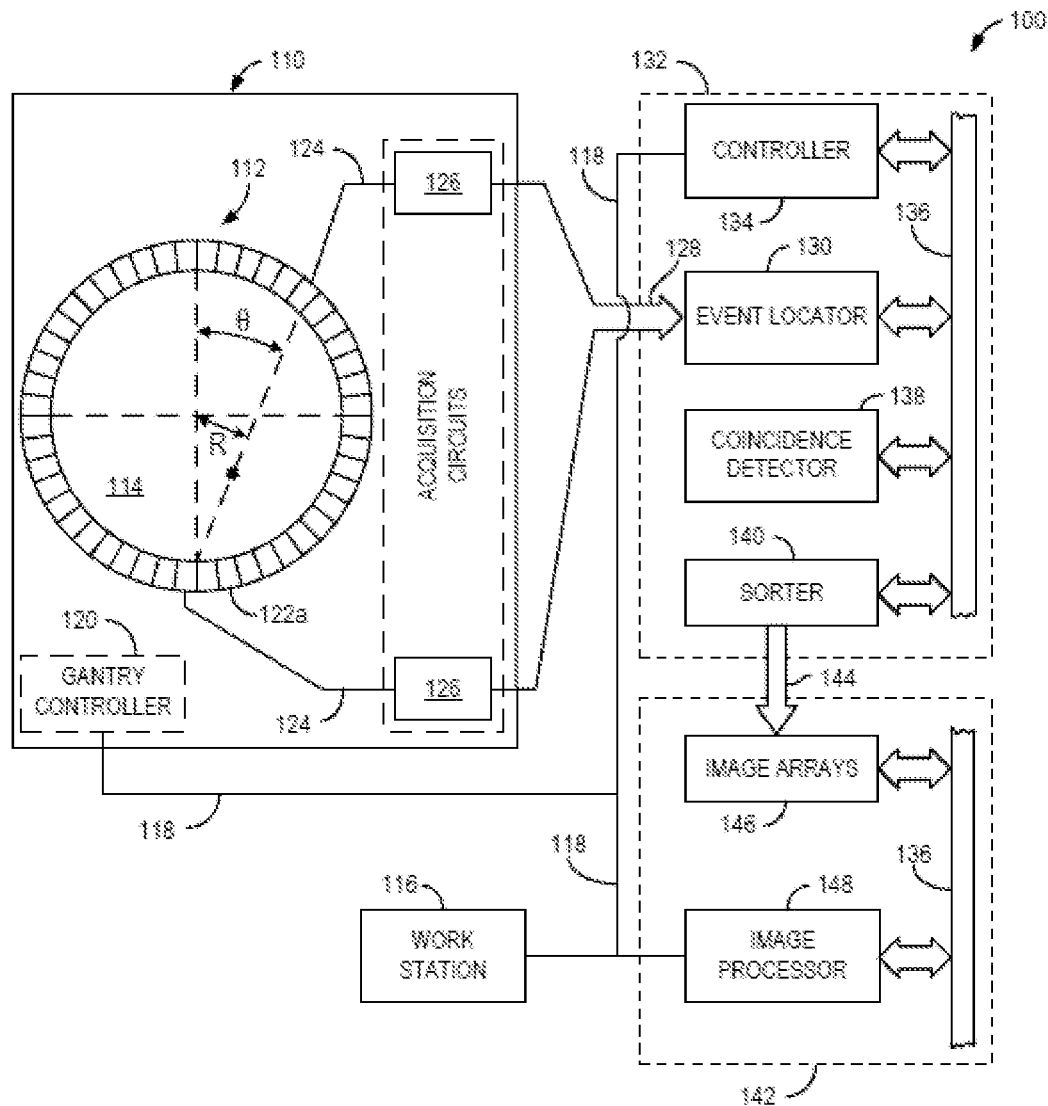
FIG. 1 is a schematic view of an emission tomography system suitable for use with the present invention.

Referring to FIG. 1, a PET system 100 that can be used in the method of present invention includes an imaging hardware system 110 that includes a detector ring assembly 112 about a central axis, or bore 114. An operator work station 116 including a commercially-available processor running a commercially-available operating system communicates through a communications link 118 with a gantry controller 120 to control operation of the imaging hardware system 110.

The detector ring assembly 112 is formed of a multitude of radiation detector units 122 that produce a signal responsive to detection of a photon on communications line 124 when an event occurs. A set of acquisition circuits 126 receive the signals and produce signals indicating the event coordinates (x, y) and the total energy associated with the photons that caused the event. These signals are sent through a cable 128 to an event locator circuit 130. Each acquisition circuit 126 also produces an event detection pulse that indicates the exact moment the interaction took place. Other systems utilize sophisticated digital electronics that can also obtain this information regarding the precise instant in which the event occurred from the same signals used to obtain energy and event coordinates.

The event locator circuits 130 in some implementations, form part of a data acquisition processing system 132 that periodically samples the signals produced by the acquisition circuits 126. The data acquisition processing system 132 includes a general controller 134 that controls communications on a backplane bus 136 and on the general communications network 118. The event locator circuits 130 assemble the information regarding each valid event into a set of numbers that indicate precisely when the event took place and the position in which the event was detected. This event data packet is conveyed to a coincidence detector 138 that is also part of the data acquisition processing system 132.

The coincidence detector 138 accepts the event data packets from the event locator circuit 130 and determines if any two of them are in coincidence. Coincidence is determined by a number of factors. First, the time markers in each event data packet must be within a predetermined time window, for example, 0.5 nanoseconds or even down to picoseconds. Second, the locations indicated by the two event data packets must lie on a straight line that passes through the field of view in the scanner bore 114. Events that cannot be paired are discarded from consideration by the coincidence detector 138, but coincident event pairs are located and recorded as a coincidence data packet. These coincidence data packets are provided to a sorter 140. The function of the sorter in many traditional PET imaging systems is to receive the coincidence data packets and generate memory addresses from the coincidence data packets for the efficient storage of the coincidence data. In that context, the set of all projection rays that point in the same direction (θ) and pass through the scanner's field of view (FOV) is a complete projection, or "view". The distance (R) between a particular projection ray and the center of the FOV locates that projection ray within the FOV. The sorter 140 counts all of the events that occur on a given projection ray (R, θ) during the scan by sorting out the coincidence data packets that indicate an event at the two detectors lying on this projection ray. The coincidence counts are organized, for example, as a set of two-dimensional arrays, one for each axial image plane, and each having as one of its dimensions the projection angle θ and the other dimension the distance R. This θ by R map of the measured events is call a histogram or, more commonly, a sinogram array. It is these sinograms that are processed to reconstruct images that indicate the number of events that took place at each image pixel location during the scan. The sorter 140 counts all events occurring along each projection ray (R, θ) and organizes them into an image data array.

The sorter 140 provides image datasets to an image processing/reconstruction system 142, for example, by way of a communications link 144 to be stored in an image array 146. The image arrays 146 hold the respective datasets for access by an image processor 148 that reconstructs images. The image processing/reconstruction system 142 may communicate with and/or be integrated with the work station 116 or other remote work stations.

The present invention provides a compound of formula (I) for use as a radiotracer with a PET system such as that shown in FIG. 1. In formula (I) below,

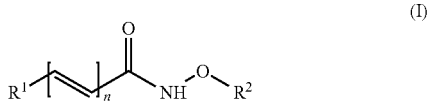

(I)

$R^1$ is a moiety including a contrast agent; $R^2$ represents hydrogen, or substituted or unsubstituted alkyl, or substituted or unsubstituted aryl, or substituted or unsubstituted heteroaryl; and n is an integer selected from 0 or 1. The term "contrast agent" herein refers to an atom or group of atoms that generate a contrasting effect in in vivo imaging techniques, whether the effect is direct and/or indirect.

The contrast agent may be a positron emitter. The positron emitter can be selected from the group consisting of $^{11}C$, $^{13}N$, $^{15}O$, $^{18}F$, $^{34m}Cl$, $^{38}K$, $^{45}Ti$, $^{51}Mn$, $^{52m}Mn$, $^{52}Fe$, $^{55}Co$, $^{60}Cu$, $^{61}Cu$, $^{62}Cu$, $^{64}Cu$, $^{66}Ga$, $^{68}Ga$, $^{71}As$, $^{72}As$, $^{74}As$, $^{75}Br$, $^{76}Br$, $^{82}Rb$, $^{86}Y$, $^{89}Zr$, $^{90}Nb$, $^{94m}Tc$, $^{110m}In$, $^{118}Sb$, $^{120}I$, $^{121}I$, $^{122}I$, and $^{124}I$. Preferably, the positron emitter is $^{11}C$ or $^{18}F$. The contrast agent may be a photon emitter. The photon emitter can be selected from the group consisting of $^{67}Ga$, $^{99m}Tc$, $^{111}In$, $^{123}I$, $^{125}I$, $^{131}I$, and $^{201}Tl$. The contrast agent may be a contrast agent for magnetic resonance imaging. The magnetic resonance imaging contrast agent can be selected from the group consisting of ions of gadolinium, manganese, and iron. The metal ion can be paramagnetic.

The compound is capable of binding to a histone deacetylase. As used herein, the term "histone deacetylase" or "HDAC" refers to a class of enzymes that have various functions in epigenetic regulation of gene expression. One function exhibited by some histone deacetylases is the removal of acetyl groups from an ε-N-acetyl lysine amino acid on a histone. Histone deacetylases may be grouped into various classes including, without limitation, class I and class II. A number of inhibitors of histone deacetylases have been identified that act on class I and class II histone deacetylases, typically by binding to the zinc-containing catalytic domain of the histone deacetylase. Certain histone deacetylase inhibitors inhibit one class, but not another class of histone deacetylases, and isoform selectivity within a class has also been observed.

The compound of formula (I) can be capable of binding to a histone deacetylase. The compound of formula (I) can be capable of specific binding to a histone deacetylase. The compound of formula (I) can be capable of pan-selective binding to a histone deacetylase. The compound of formula (I) can be capable of class-selective binding to a histone deacetylase. The compound of formula (I) can be capable of class I-selective binding to a histone deacetylase. The compound of formula (I) can be capable of class II-selective binding to a histone deacetylase. The compound of formula (I) can be capable of isoform-selective binding to a histone deacetylase. The compound of formula (I) can be a class I-specific histone deacetylase inhibitor. The compound of formula (I) can be a class II-specific histone deacetylase inhibitor. The compound of formula (I) can be an isoform-specific histone deacetylase inhibitor. The compound of formula (I) can be capable of class-selective and isoform-selective binding to a histone deacetylase. The binding to the histone deacetylase can be reversible.

The compound of formula (I) has an octanol-water partition coefficient (log D) in the range of 1 to 3, preferably 1.8 to 2.2, indicating that the compound of formula (I) can cross the blood-brain barrier. The compound can have a brain to plasma ratio greater than 1, indicating that the compound of formula (I) can cross the blood-brain barrier. In one version of the compound of formula (I), $R^2$ represents hydrogen. In one version of the compound of formula (I), $R^1$ is a moiety including a substituted or unsubstituted adamantyl (tricyclo [3.3.1.1$^{3,7}$]decyl) group. In one version of the compound of formula (I), n is 1. When n is 1, $R^1$ may be selected from the group consisting of

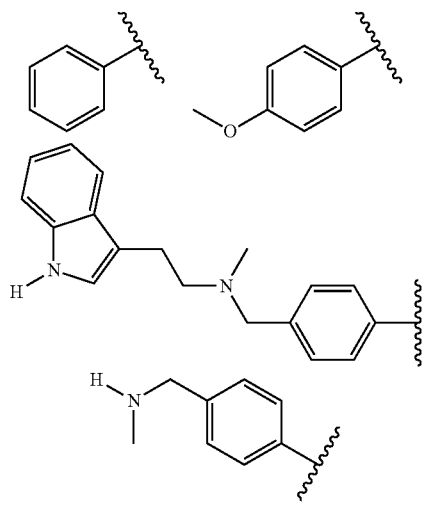

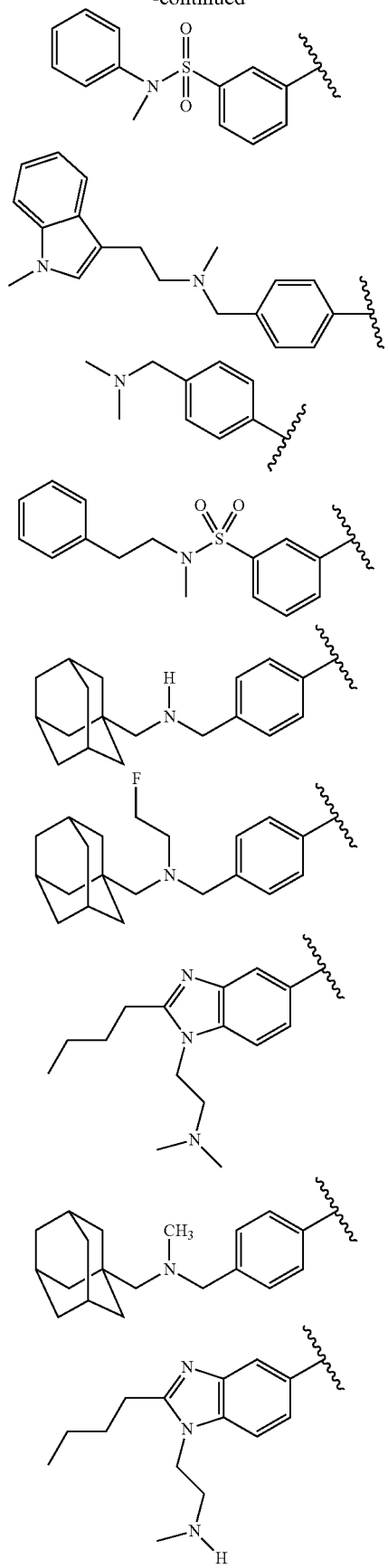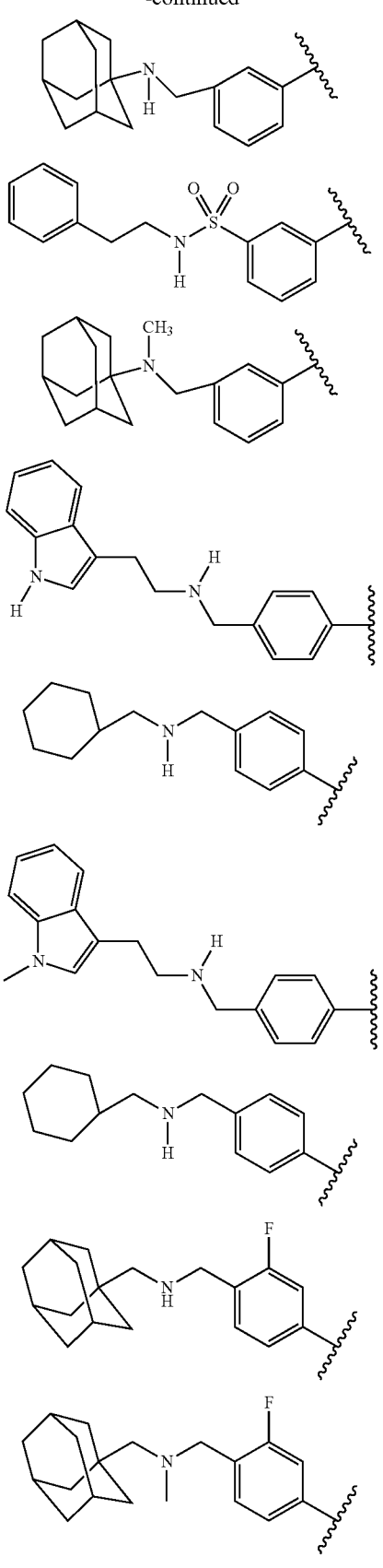

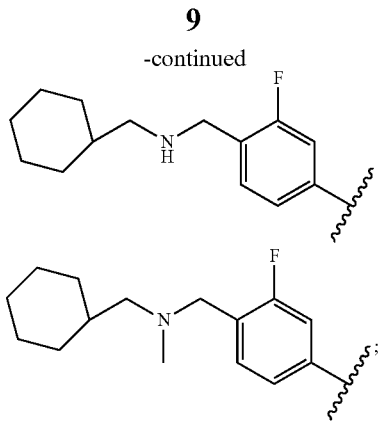

and at least one atom in $R^1$ is replaced with a positron emitter selected from the group consisting of $^{11}C$, $^{13}N$, $^{15}O$, $^{18}F$, $^{34m}Cl$, $^{38}K$, $^{45}Ti$, $^{51}Mn$, $^{52m}Mn$, $^{52}Fe$, $^{55}Co$, $^{60}Cu$, $^{61}Cu$, $^{62}Cu$, $^{64}Cu$, $^{66}Ga$, $^{68}Ga$, $^{71}As$, $^{72}As$, $^{74}As$, $^{75}Br$, $^{76}Br$, $^{82}Rb$, $^{86}Y$, $^{89}Zr$, $^{90}Nb$, $^{94m}Tc$, $^{110m}In$, $^{118}Sb$, $^{120}I$, $^{121}I$, $^{122}I$, and $^{124}I$.

In one version of the compound of formula (I), the compound is

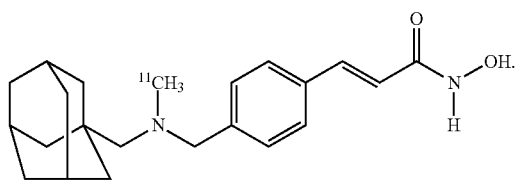 [SMILES: [11CH3]N(Cc1ccc(/C=C/C(=O)NO)cc1)CC12CC3CCC(CC(C3)C1)C2]

In one version of the compound of formula (I), n is 0. When n is 0, $R^1$ may be selected from the group consisting of

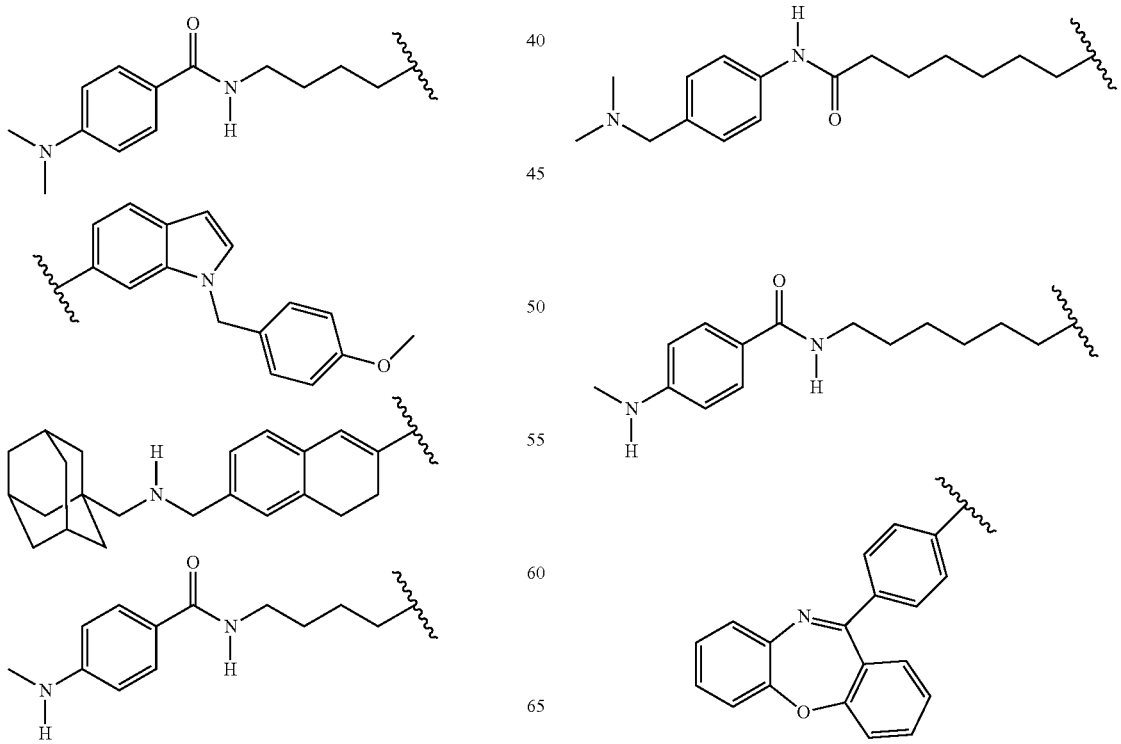

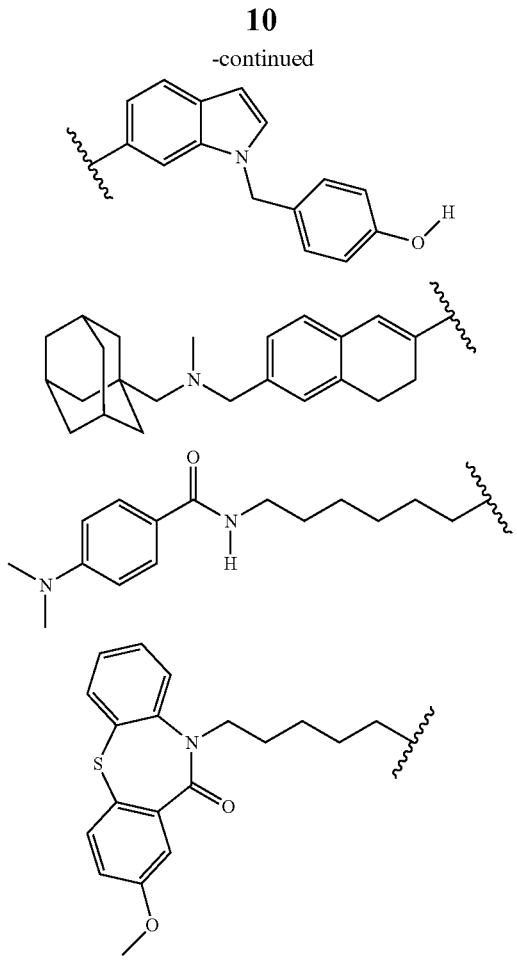

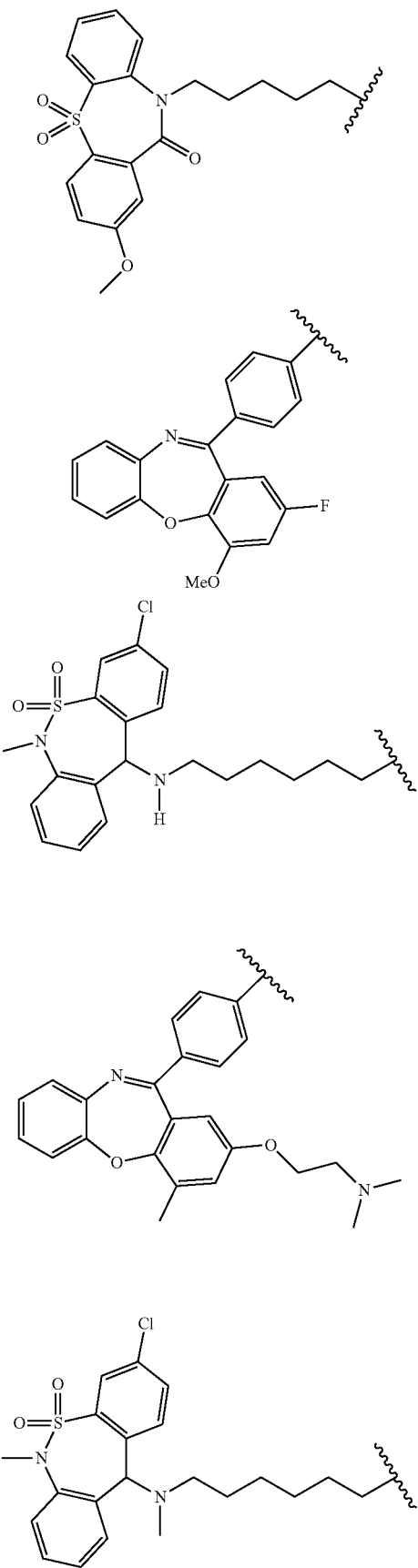

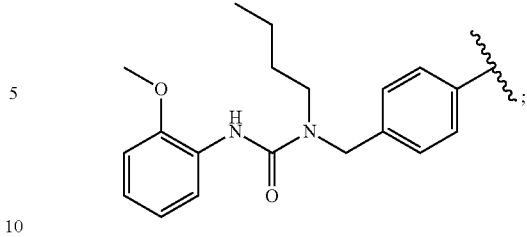

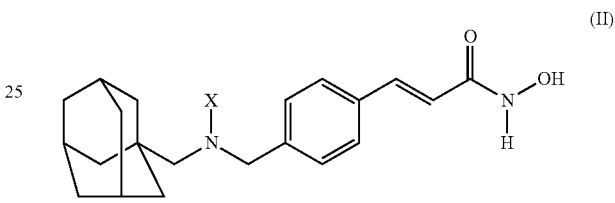

and at least one atom in $R^1$ is replaced with a positron emitter selected from the group consisting of $^{11}C$, $^{13}N$, $^{15}O$, $^{18}F$, $^{34m}Cl$, $^{38}K$, $^{45}Ti$, $^{51}Mn$, $^{52m}Mn$, $^{52}Fe$, $^{55}Co$, $^{60}Cu$, $^{61}Cu$, $^{62}Cu$, $^{64}Cu$, $^{66}Ga$, $^{68}Ga$, $^{71}As$, $^{72}As$, $^{74}As$, $^{75}Br$, $^{76}Br$, $^{82}Rb$, $^{86}Y$, $^{89}Zr$, $^{90}Nb$, $^{94m}Tc$, $^{110m}In$, $^{118}Sb$, $^{120}I$, $^{121}I$, $^{122}I$, and $^{124}I$.

The invention also provides a compound of formula (II) below:

(II)

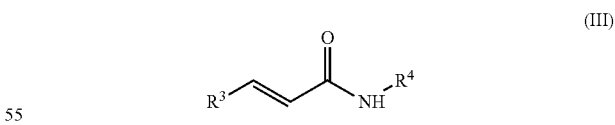

wherein X represents a moiety other than hydrogen. X can represent substituted or unsubstituted alkyl, substituted or unsubstituted aryl, substituted or unsubstituted heteroaryl, or substituted or unsubstituted heterocyclic. The compound of formula (II) is capable of specific binding to a histone deacetylase. In one version of the compound of formula (II), at least one atom in the compound is replaced with a contrast agent. In one version of the compound of formula (II), at least one atom in the compound is replaced with a positron emitter. The positron emitter may be selected from the group consisting of $^{11}C$, $^{13}N$, $^{15}O$, $^{18}F$, $^{34m}Cl$, $^{38}K$, $^{45}Ti$, $^{51}Mn$, $^{52m}Mn$, $^{52}Fe$, $^{55}Co$, $^{60}Cu$, $^{61}Cu$, $^{62}Cu$, $^{64}Cu$, $^{66}Ga$, $^{68}Ga$, $^{71}As$, $^{72}As$, $^{74}As$, $^{75}Br$, $^{76}Br$, $^{82}Rb$, $^{86}Y$, $^{89}Zr$, $^{90}Nb$, $^{94m}Tc$, $^{110m}In$, $^{118}Sb$, $^{120}I$, $^{121}I$, $^{122}I$, and $^{124}I$, is $^{11}C$ or $^{18}F$. In one version of the compound of formula (II), X is methyl. In one version of the compound of formula (II), X is $^{11}CH_3$.

The invention also provides a compound of formula (III) below:

(III)

$$R^3 \overset{O}{\underset{NH}{\diagdown}} R^4$$

wherein $R^3$ is a moiety including a contrast agent, and
wherein $R^4$ represents hydrogen, or substituted or unsubstituted alkyl, or substituted or unsubstituted aryl, substituted or unsubstituted heteroaryl, or substituted or unsubstituted heterocyclic.

The contrast agent may be a positron emitter. The positron emitter can be selected from the group consisting of $^{11}C$, $^{13}N$, $^{15}O$, $^{18}F$, $^{34m}Cl$, $^{38}K$, $^{45}Ti$, $^{51}Mn$, $^{52m}Mn$, $^{52}Fe$, $^{55}Co$, $^{60}Cu$, $^{61}Cu$, $^{62}Cu$, $^{64}Cu$, $^{66}Ga$, $^{68}Ga$, $^{71}As$, $^{72}As$, $^{74}As$, $^{75}Br$, $^{76}Br$, $^{82}Rb$, $^{86}Y$, $^{89}Zr$, $^{90}Nb$, $^{94m}Tc$, $^{110m}In$, $^{118}Sb$, $^{120}I$, $^{121}I$, $^{122}I$, and $^{124}I$. Preferably, the positron emitter is $^{11}C$ or $^{18}F$.

The contrast agent may be a photon emitter. The photon emitter can be selected from the group consisting of $^{67}$Ga, $^{99m}$Tc, $^{111}$In, $^{123}$I, $^{125}$I, and $^{201}$Tl. The contrast agent may be a contrast agent for magnetic resonance imaging. The magnetic resonance imaging contrast agent can be selected from the group consisting of ions of gadolinium, manganese, and iron. The metal ion can be paramagnetic.

The compound of formula (III) can be capable of binding to a histone deacetylase. The compound of formula (III) can be capable of specific binding to a histone deacetylase. The compound of formula (III) can be capable of pan-selective binding to a histone deacetylase. The compound of formula (III) can be capable of class-selective binding to a histone deacetylase. The compound of formula (III) can be capable of class I-selective binding to a histone deacetylase. The compound of formula (III) can be capable of class II-selective binding to a histone deacetylase. The compound of formula (III) can be capable of isoform-selective binding to a histone deacetylase. The compound of formula (III) can be a class I-specific histone deacetylase inhibitor. The compound of formula (III) can be a class II-specific histone deacetylase inhibitor. The compound of formula (III) can be an isoform-specific histone deacetylase inhibitor. The compound of formula (III) can be capable of class-selective and isoform-selective binding to a histone deacetylase. The binding to the histone deacetylase can be reversible.

In the compound of formula (III), $R^3$ can be a moiety including a substituted or unsubstituted adamantyl group. $R^3$ can be

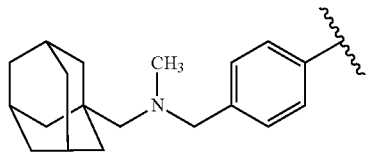 [SMILES: *c1ccc(CN(C)CC23CC4CC(CC(C4)C2)C3)cc1]

; wherein at least one atom in $R^3$ is replaced with a positron emitter selected from the group consisting of $^{11}$C, $^{13}$N, $^{15}$O, $^{18}$F, $^{34m}$Cl, $^{38}$K, $^{45}$Ti, $^{51}$Mn, $^{52m}$Mn, $^{52}$Fe, $^{55}$Co, $^{60}$Cu, $^{61}$Cu, $^{62}$Cu, $^{64}$Cu, $^{66}$Ga, $^{68}$Ga, $^{71}$As, $^{72}$As, $^{74}$As, $^{75}$Br, $^{76}$Br, $^{82}$Rb, $^{86}$Y, $^{89}$Zr, $^{90}$Nb, $^{94m}$Tc, $^{110m}$In, $^{118}$Sb, $^{120}$I, $^{121}$I, $^{122}$I, and $^{124}$I.

In the compound of formula (III), $R^4$ can be selected from the group consisting of

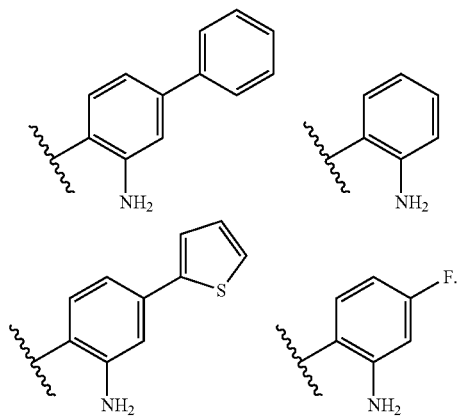

The invention also provides a method for in vivo imaging of a subject. The method includes the steps of: (a) administering to the subject the compound of formula (I) or the compound of formula (II) or the compound of formula (III); (b) waiting a time sufficient to allow the compound to accumulate at a tissue or cell site to be imaged; and (c) imaging the cells or tissues with a non-invasive imaging technique. The non-invasive imaging technique may be positron emission tomography imaging, or positron emission tomography with computed tomography imaging, or positron emission tomography with magnetic resonance imaging.

The invention also provides a method of imaging a subject by emission tomography. The method includes the steps of: (a) administering the compound of formula (I) or the compound of formula (II) or the compound of formula (III) to the subject; (b) using a plurality of detectors to detect gamma rays emitted from the subject and to communicate signals corresponding to the detected gamma rays; and (c) reconstructing from the signals a series of medical images of a region of interest of the subject.

The invention also provides an imaging method comprising acquiring an image of a human patient to whom a detectable amount of the compound of formula (I) or the compound of formula (II) has been administered. The method may comprise acquiring a brain image of the patient using positron emission tomography imaging, positron emission tomography with computed tomography imaging, or positron emission tomography with magnetic resonance imaging. The detectable amount of the compound is an amount of the compound that is sufficient to enable detection of accumulation of the compound in cells or tissue by a medical imaging technique.

The invention also provides a method for evaluating epigenetic regulation in a subject. The method includes the steps of: (a) administering to the subject the compound of formula (I) or the compound of formula (II) or the compound of formula (III); (b) waiting a time sufficient to allow the compound to accumulate at a tissue or cell site to be imaged; and (c) imaging the cells or tissues with a non-invasive imaging technique. The tissue or cell site may be in the brain. The non-invasive imaging technique may be positron emission tomography imaging, positron emission tomography with computed tomography imaging, or positron emission tomography with magnetic resonance imaging. In the method, one may allow the compound to bind to histone deacetylase at the tissue or cell site to be imaged.

The invention also provides a method for detecting histone deacetylase in a subject. The method includes the steps of: (a) administering to the subject the compound of formula (I) or the compound of formula (II) or the compound of formula (III); (b) waiting a time sufficient to allow the compound to accumulate at a tissue or cell site to be imaged; and (c) imaging the cells or tissues with a non-invasive imaging technique. The tissue or cell site may be in the brain. The non-invasive imaging technique may be positron emission tomography imaging, or positron emission tomography with computed tomography imaging, or positron emission tomography with magnetic resonance imaging. In the method, one may allow the compound to bind to histone deacetylase at the tissue or cell site to be imaged.

The invention also provides a method for imaging histone deacetylase in a subject. The method comprises (a) administering to the subject a compound having a measurable rate constant for binding ($k_{on}$) to histone deacetylase of less than 0.25 min$^{-1}$ μM$^{-1}$; (b) waiting a time sufficient to allow the compound to accumulate at a tissue or cell site to be imaged;

and (c) imaging the cells or tissues with a non-invasive imaging technique. The compound can have a rate constant for release ($k_{off}$) from histone deacetylase in the range of 0.001 min$^{-1}$ to 0.2 min$^{-1}$. Preferably, the compound having these $k_{on}$ and $k_{off}$ values is of formula (II) below:

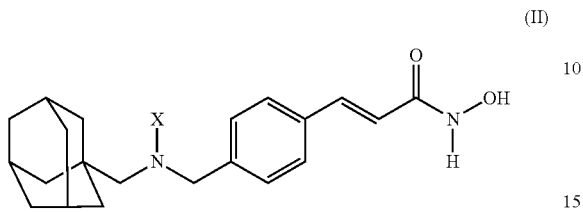

(II)

wherein X represents a moiety other than hydrogen. X can represent substituted or unsubstituted alkyl, substituted or unsubstituted aryl, substituted or unsubstituted heteroaryl, or substituted or unsubstituted heterocyclic. In one version of the compound of formula (II), X is methyl.

The invention also provides a method for the treatment of a condition involving a histone deacetylase. The method comprises administering to a subject having the condition a therapeutically effective amount of a compound of formula (I):

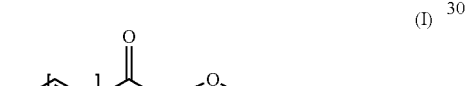

(I)

wherein R$^1$ represents hydrogen, or substituted or unsubstituted alkyl, or substituted or unsubstituted aryl, substituted or unsubstituted heteroaryl, or substituted or unsubstituted heterocyclic, wherein R$^2$ represents hydrogen, or substituted or unsubstituted alkyl, or substituted or unsubstituted aryl, substituted or unsubstituted heteroaryl, or substituted or unsubstituted heterocyclic, and wherein n is an integer selected from 0 or 1. The condition may a psychiatric disorder or a neurological disorder or cancer or heart disease, or an inflammatory disease.

In the method for the treatment of a condition involving a histone deacetylase, the compound can have formula (II):

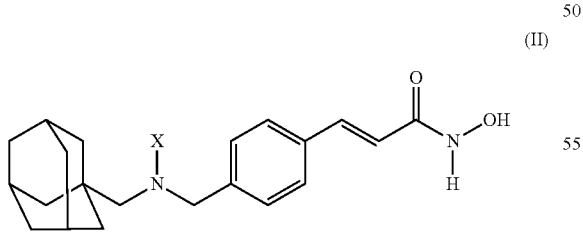

(II)

wherein X represents a moiety other than hydrogen. X can represent substituted or unsubstituted alkyl, substituted or unsubstituted aryl, substituted or unsubstituted heteroaryl or substituted or unsubstituted heterocyclic. X can be methyl.

In the method for the treatment of a condition involving a histone deacetylase, R$^1$ in the compound of formula (I) can be selected from the group consisting of

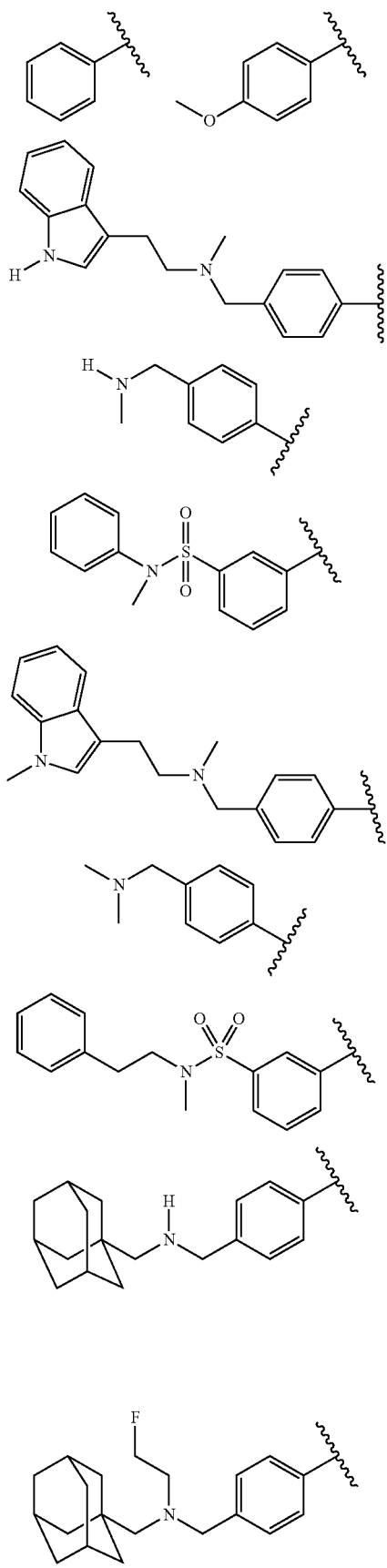

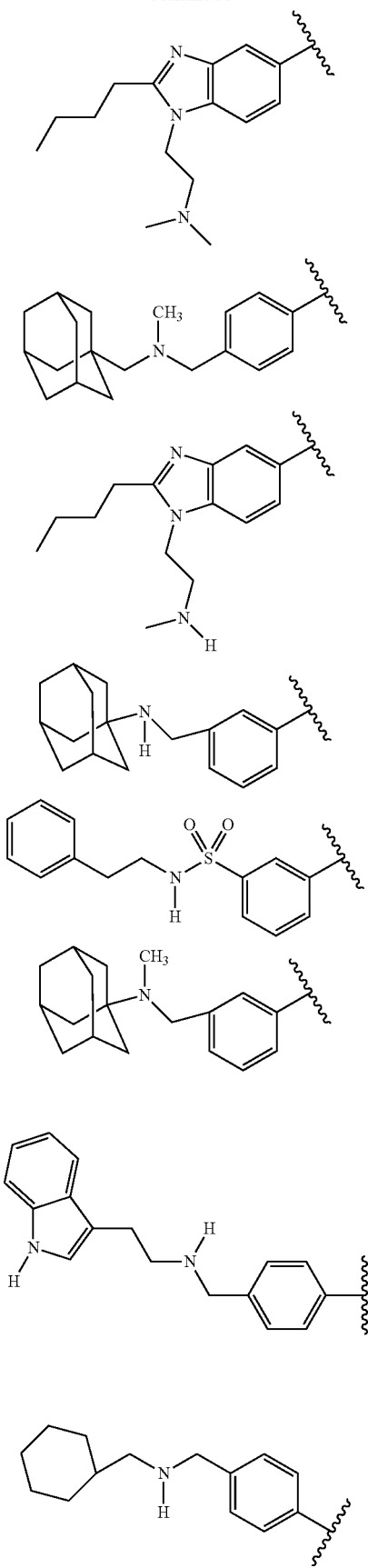
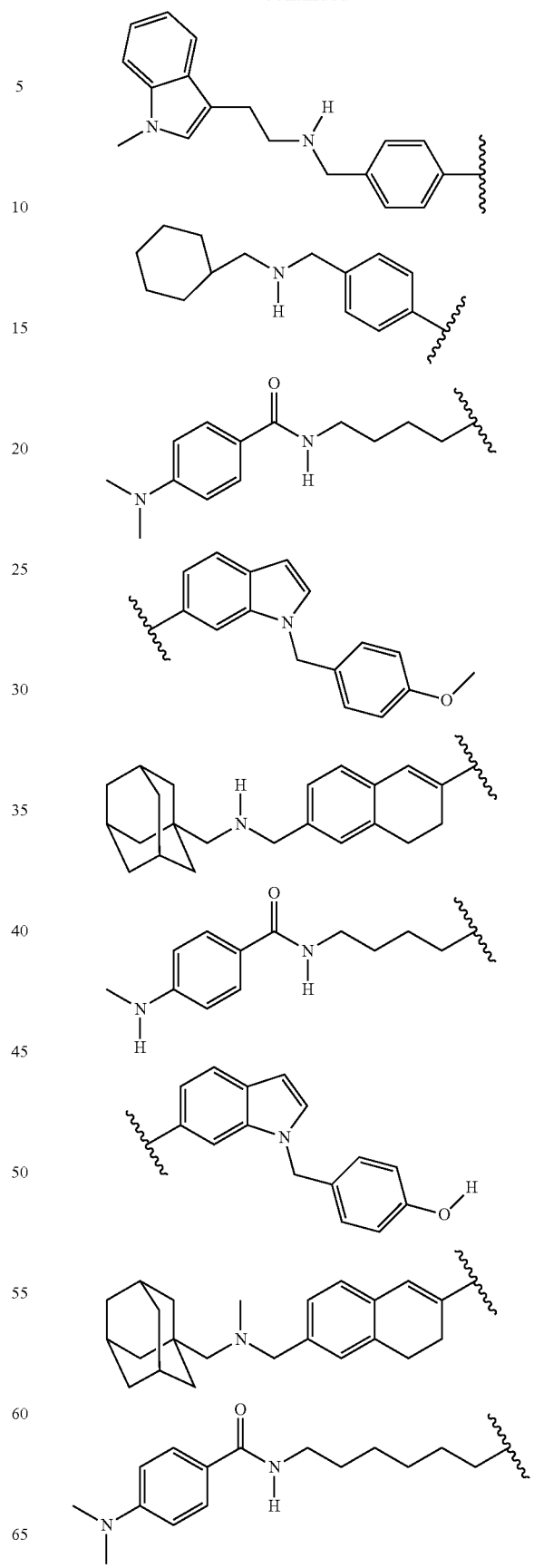

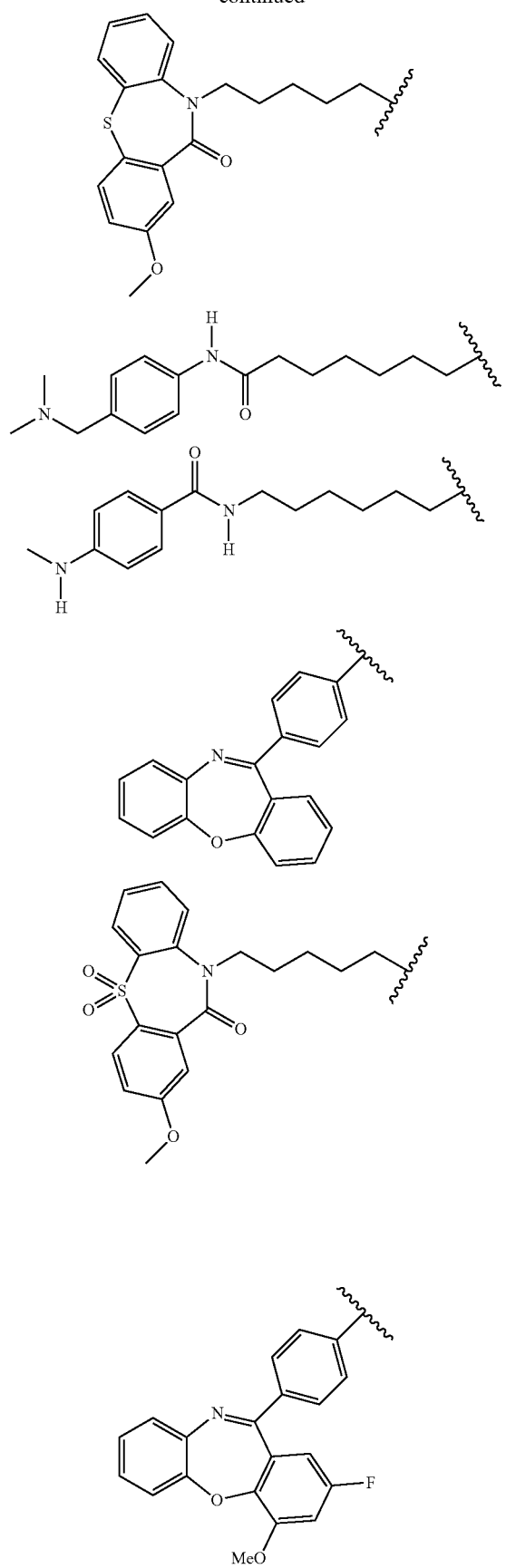
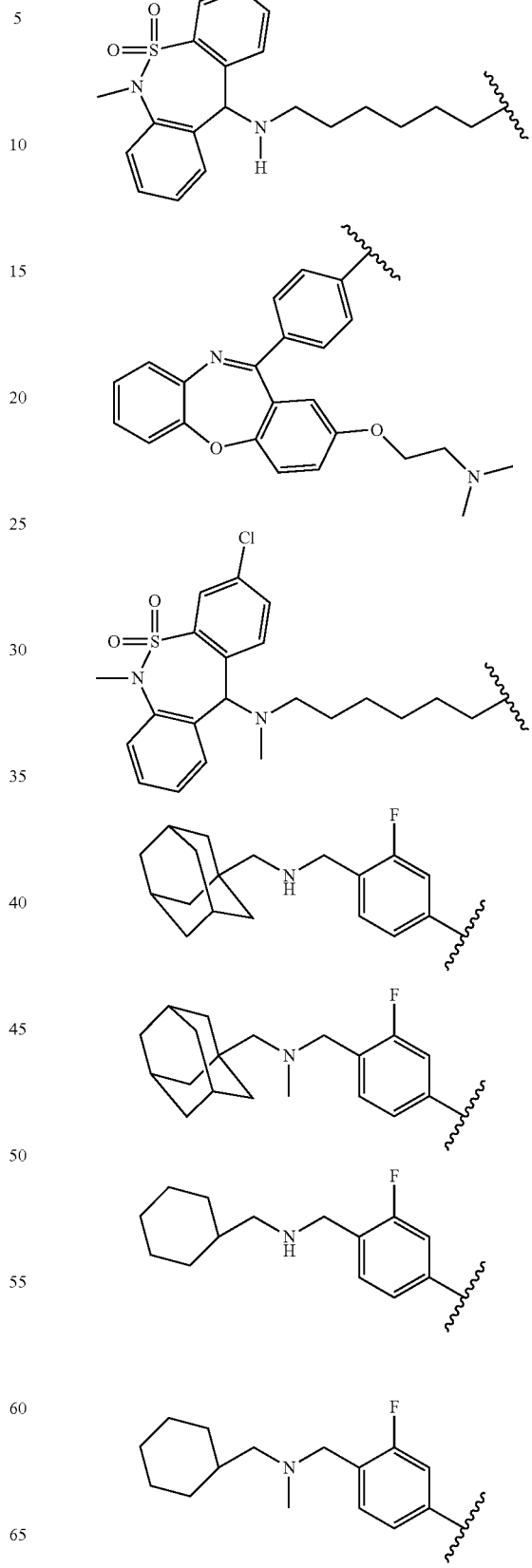

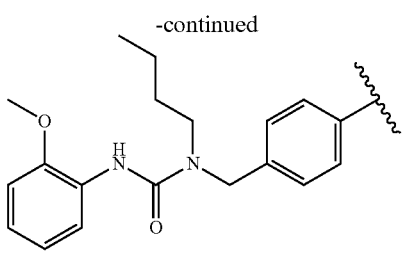

The invention also provides a method for the treatment of a condition involving a histone deacetylase. The method comprises administering to a subject having the condition a therapeutically effective amount of a compound of formula (III) below:

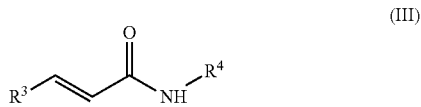

wherein $R^3$ is represents hydrogen, or substituted or unsubstituted alkyl, or substituted or unsubstituted aryl, substituted or unsubstituted heteroaryl, or substituted or unsubstituted heterocyclic, and wherein $R^4$ represents hydrogen, or substituted or unsubstituted alkyl, or substituted or unsubstituted aryl, substituted or unsubstituted heteroaryl, or substituted or unsubstituted heterocyclic.

In the compound of formula (III), $R^3$ can be a moiety including a substituted or unsubstituted adamantyl group. $R^3$ can be

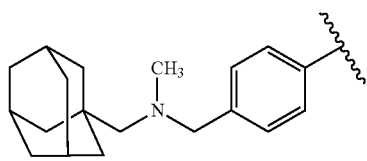 [SMILES: *c1ccc(CN(C)CC23CC4CC(CC(C4)C2)C3)cc1]

In the compound of formula (III), $R^4$ can be selected from the group consisting of

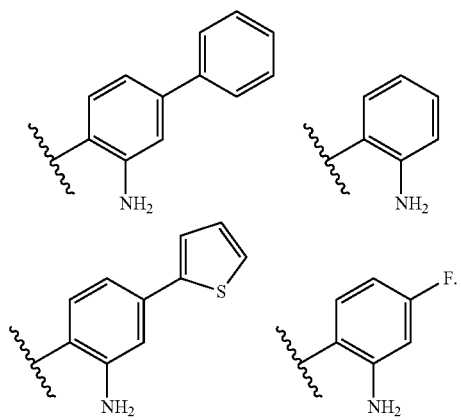

A "therapeutically effective amount" means an amount of a composition that, when administered to a subject for treating the condition, is sufficient to effect such treatment for the condition. The "therapeutically effective amount" will vary depending on the composition, the condition state being treated, the severity of the condition treated, the age and relative health of the subject, the route and form of administration, the judgment of the attending medical or veterinary practitioner, and other factors. Those skilled in the art are readily able to determine therapeutically effective amount by administering a compound of the invention to a subject in increasing amounts until the condition is treated.

The invention also provides an emission tomography system for acquiring a series of medical images of a subject during an imaging process using a radiotracer. The system includes a plurality of detectors configured to be arranged about the subject to acquire gamma rays emitted from the subject over a time period relative to an administration of the radiotracer to the subject and communicate signals corresponding to acquired gamma rays; a data processing system configured to receive the signals from the plurality of detectors; and a reconstruction system configured to receive the signals from the data processing system and reconstruct therefrom a series of medical images of the subject. The radiotracer may be any of the compounds of formula (I) or the compounds of formula (II) or the compounds of formula (III).

Below are non-limiting examples of compounds suitable for radioisotopic labeling such that the radiolabeled compounds can be used in the method of the invention with a PET system such as that shown in FIG. 1. Compound numbers are provided below the compounds for ease of reference. At least one atom in each of these compounds can be replaced with a positron emitter, such as $^{11}C$, $^{13}N$, $^{15}O$, $^{18}F$, $^{34m}Cl$, $^{38}K$, $^{45}Ti$, $^{51}Mn$, $^{52m}Mn$, $^{52}Fe$, $^{55}Co$, $^{60}Cu$, $^{61}Cu$, $^{62}Cu$, $^{64}Cu$, $^{66}Ga$, $^{68}Ga$, $^{71}As$, $^{72}As$, $^{74}As$, $^{75}Br$, $^{76}Br$, $^{82}Rb$, $^{86}Y$, $^{89}Zr$, $^{90}Nb$, $^{94m}Tc$, $^{110m}In$, $^{118}Sb$, $^{120}I$, $^{121}I$, $^{122}I$, and $^{124}I$.

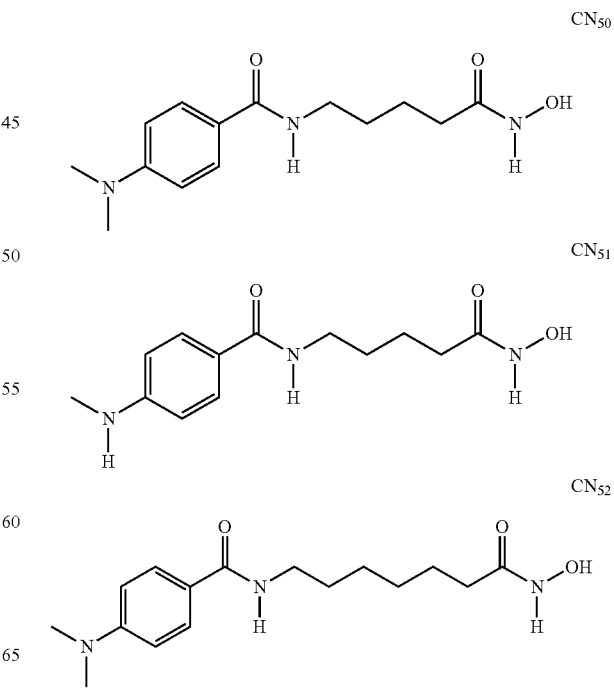

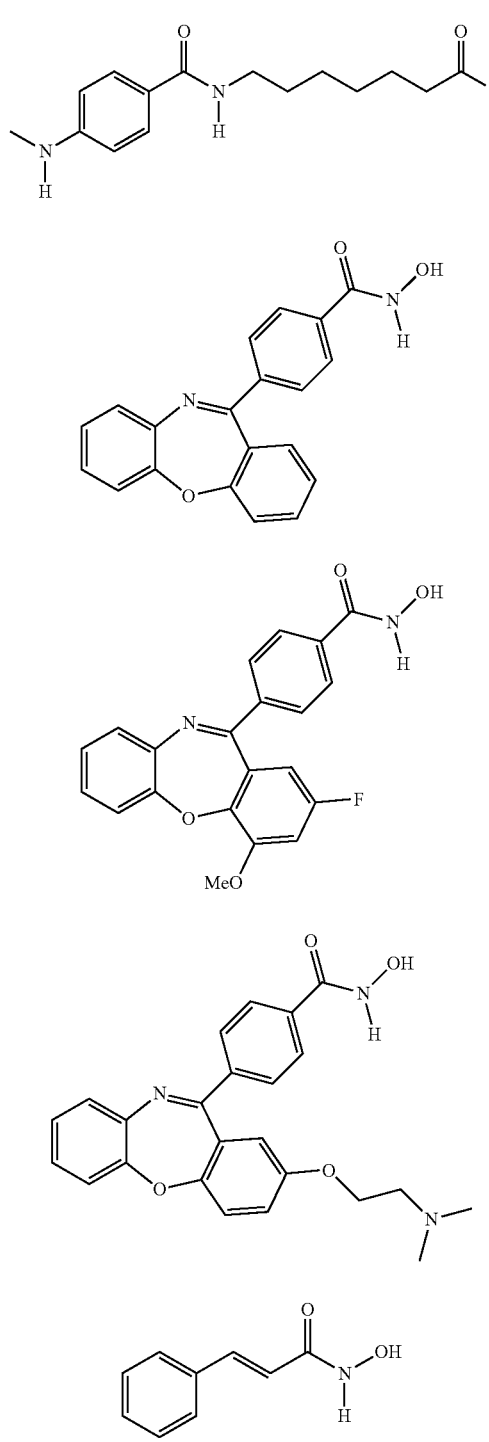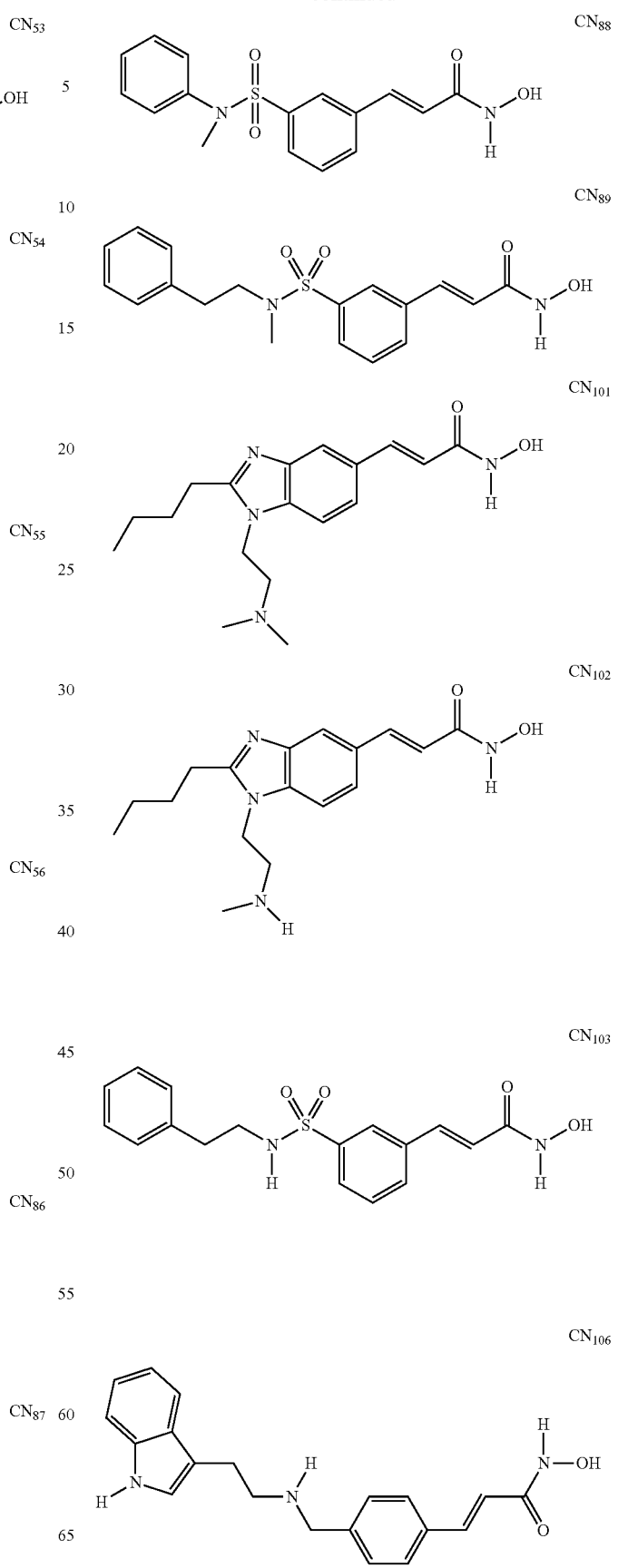

CN107
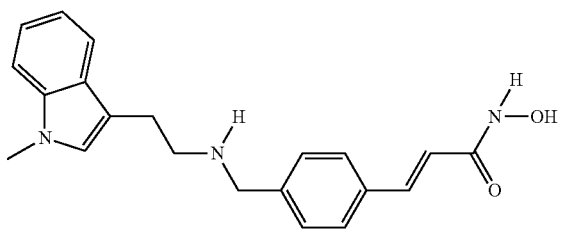
CN108
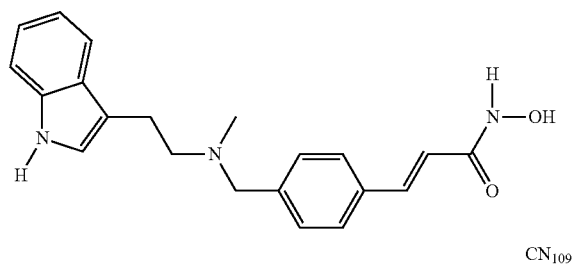
CN109
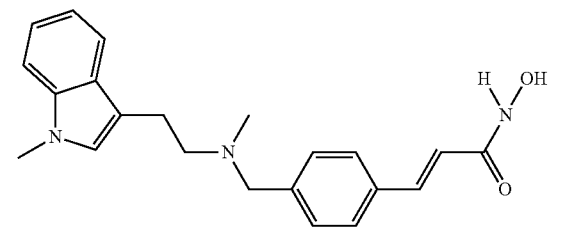
CN110
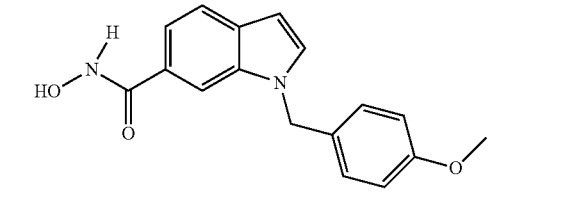
CN111
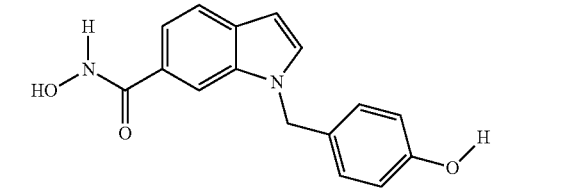
CN112
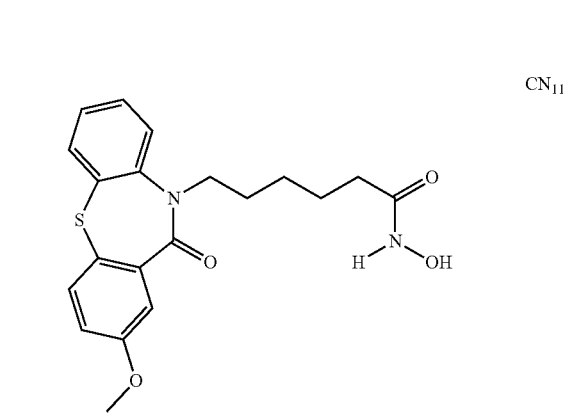
CN113
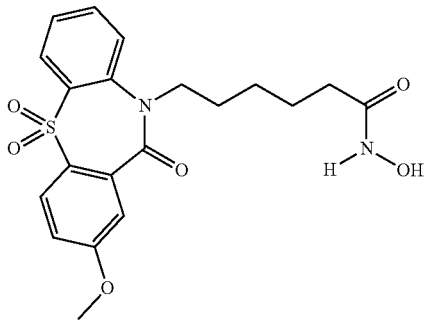
CN132
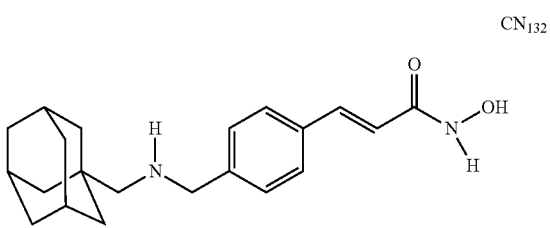
CN133
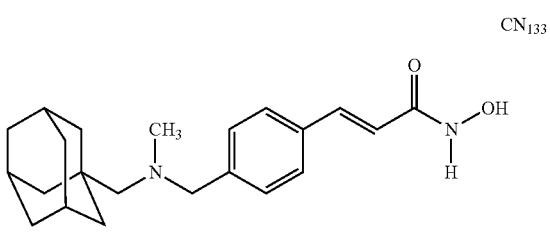
CN136
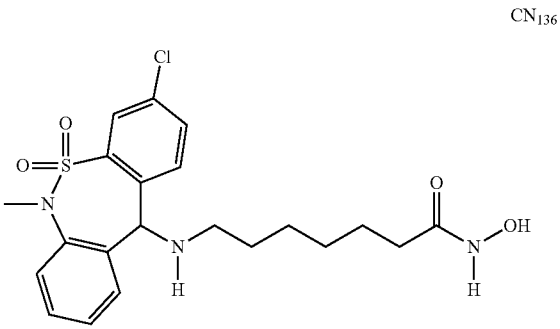
CN137
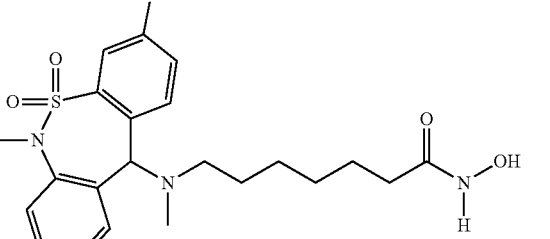
CN138
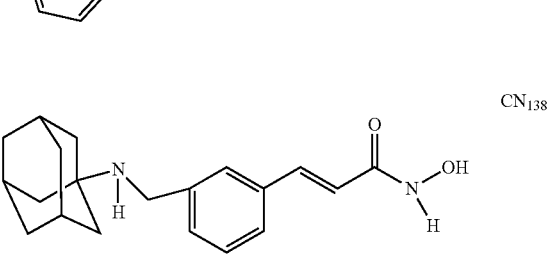

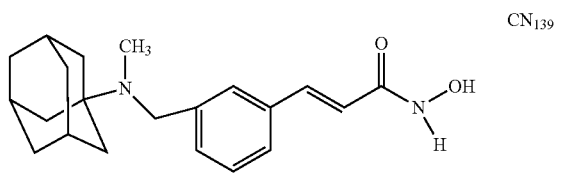
CN139

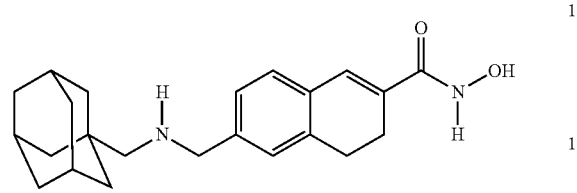
CN140

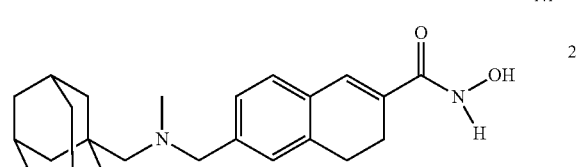
CN141

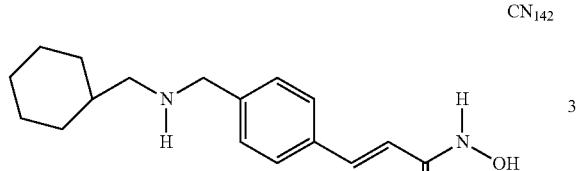
CN142

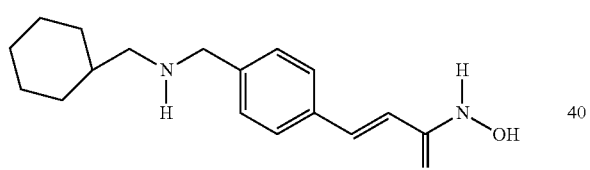
CN143

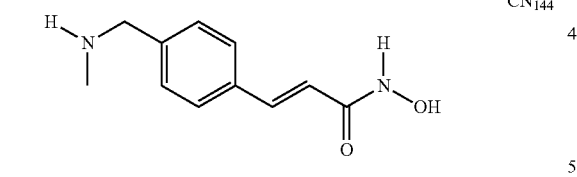
CN144

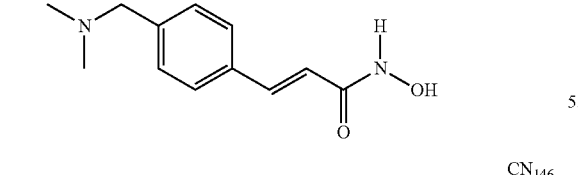
CN145

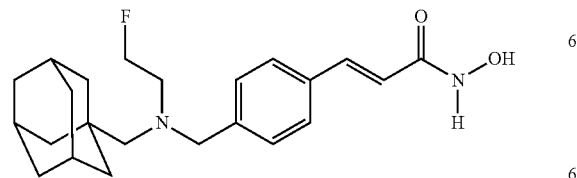
CN146

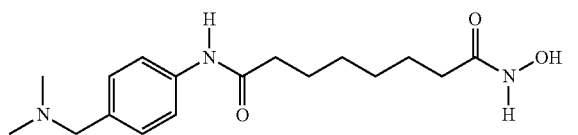
CN30

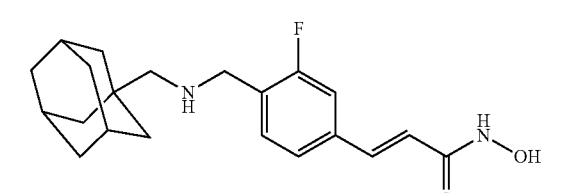
CN148

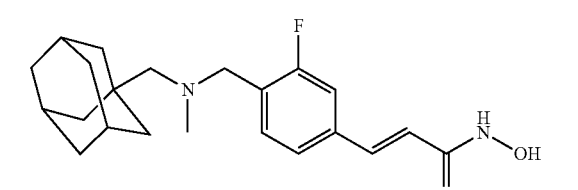
CN149

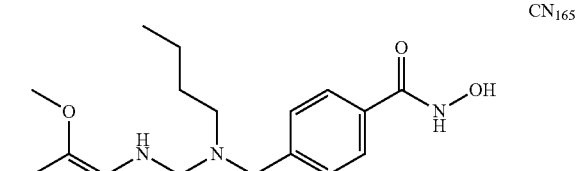
CN165

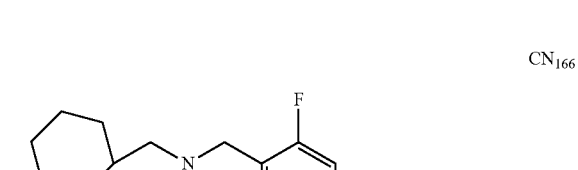
CN166

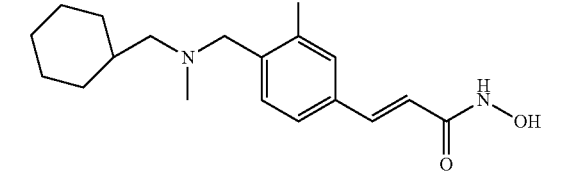
CN167

Below are non-limiting examples of tool compounds suitable for development as therapeutic leads such that the radiolabeled imaging agents can be used in the method of the invention with a PET system such as that shown in FIG. 1 to assess the tissue- and region-specific target engagement of the tool compound via blocked binding of the imaging agent. Compound numbers are provided below the compounds for ease of reference.

CN147

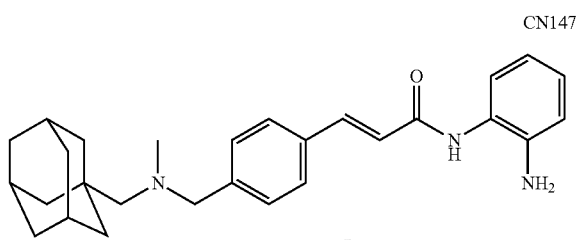

Chemical Formula: C$_{28}$H$_{35}$N$_3$O
Exact Mass: 429.28
Molecular Weight: 429.60
Log P: 4.63
IPSA: 56.36
CLogP: 6.589

CN161

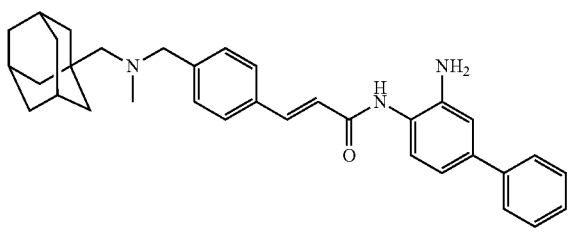

(E)-3-(4-((((3r,5r,7r)-adamantan-1-ylmethyl)(methyl)amino)
methyl)phenyl)-N-(3-amino-[1,1'-biphenyl]-4-yl)acrylamide
Exact Mass: 505.309
Molecular Weight: 505.893

CN162

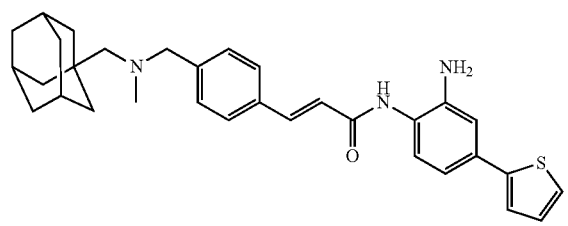

(E)-3-(4-((((3r,5r,7r)-adamantan-1-yl)methyl)(methyl)amino)
methyl)phenyl)-N-(2-amino-4-(thiophen-2-yl)phenyl)acrylamide
Exact Mass: 511.266
Molecular Weight: 511.721

CN163

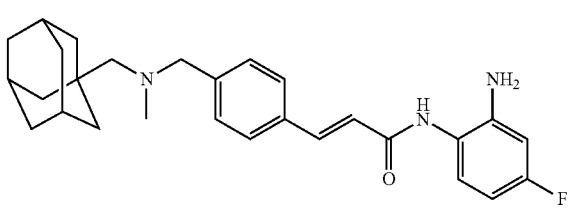

(E)-3-(4-((((3r,5r,7r)-adamantan-1-ylmethyl)(methyl)amino)
methyl)phenyl)-N-(2-amino-4-fluorophenyl)acrylamide
Exact Mass: 447.269
Molecular Weight: 447.597

The compound of formula (I) or the compound of formula (II) or the compound of formula (III) is targeted to histone deacetylase in the subject. Administration to the patient of a detectable amount of a pharmaceutical composition including the compound of formula (I) or the compound of formula (II) or the compound of formula (III) for in vivo detection of histone deacetylase can be accomplished intravenously, intraarterially, intrathecally, intramuscularly, intradermally, subcutaneously, or intracavitary. Dosage can vary from 0.001 µg/kg to 10 µg/kg. In the method of the invention, sufficient time is allowed after administration such that the compound of formula (I) or the compound of formula (II) or the compound of formula (III) can bind histone deacetylase in the subject. A "detectable amount" means that the amount of the detectable compound that is administered is sufficient to enable detection of the compound in the subject by a medical imaging technique.

The invention is further illustrated in the following Examples which are presented for purposes of illustration and not of limitation.

EXAMPLES

Development of histone deacetylase imaging agents for non-invasive PET imaging is important in elucidating the distribution and expression of histone deacetylase enzymes and their roles in diseases, including brain disorders, tumors and heart disease, also can be used for diagnosing such diseases in their early stage and accelerate the drug development. In this non-limiting example, we show that a hydroxamic acid-based small-molecule (E)-3-(4-((((3r,5r,7r)-adamantan-1-ylmethyl)(methyl)amino)methyl)phenyl)-N-hydroxyacrylamide (referred to as "CN133" herein) shows high binding to histone deacetylases. With the carbon-11 incorporation, [$^{11}$C]CN133 exhibits high brain uptake and high specific binding in rodents and non-human primates, also shows blockade by pretreating with HDAC inhibitors in the peripheral organs. These results indicate that [$^{11}$C]CN133 is a universal PET imaging probe for histone deacetylases, and it is contemplated that human evaluations will demonstrate that [$^{11}$C]CN133 and related hydroxamates are the first tools available to study epigenetic regulation in inaccessible human tissue.

General Methods and Materials

All reagents and solvents were of ACS-grade purity or higher and used without further purification. NMR data were recorded on a Varian 500 MHz magnet and were reported in ppm units downfield from trimethylsilane. Analytical separation was conducted on an Agilent 1100 series HPLC fitted with a diode-array detector, quaternary pump, vacuum degasser, and autosampler. Mass spectrometry data were recorded on an Agilent 6310 ion trap mass spectrometer (ESI source) connected to an Agilent 1200 series HPLC with quaternary pump, vacuum degasser, diode-array detector, and autosampler. $^{11}$CH$_4$ (1.2 Ci) was obtained via the $^{14}$N(p,α)$^{11}$C reaction on nitrogen with 2.5% oxygen, with 11 MeV protons (Siemens Eclipse cyclotron), and trapped on molecular sieves in a TRACERlab FX-Mel synthesizer (General Electric). $^{11}$CH$_4$ was obtained by the reduction of $^{11}$CO$_2$ in the presence of Ni/hydrogen at 350° C. and recirculated through an oven containing I$_2$ to produce $^{11}$CH$_3$I via a radical reaction.

MR-PET imaging was performed in anesthetized (ketamine, isoflurane) baboon (*papio anubis*) to minimize discomfort. Highly-trained animal technicians monitored animal safety throughout all procedures and veterinary staff were responsible for daily care. All animals were socially housed in cages appropriate for the physical and behavioral health of the individual animal. Animals were fed thrice per diem, with additional nutritional supplements provided as prescribed by the attending veterinarian. Audio, video and tactile enrichment was provided on a daily basis to promote psychological well-being. No non-human primates were euthanized to accomplish the research presented.

PET/CT imaging was performed in anesthetized (isoflurane) rats (Sprague Dawley) to minimize discomfort. Highly-trained animal technicians monitored animal safety throughout all procedures and veterinary staff were responsible for daily care. All animals were socially housed in cages appropriate for the physical and behavioral health of the individual animal. Animals were given unlimited access to food and water, with additional nutritional supplements provided as prescribed by the attending veterinary staff.

Chemical Synthesis

Figure 2:
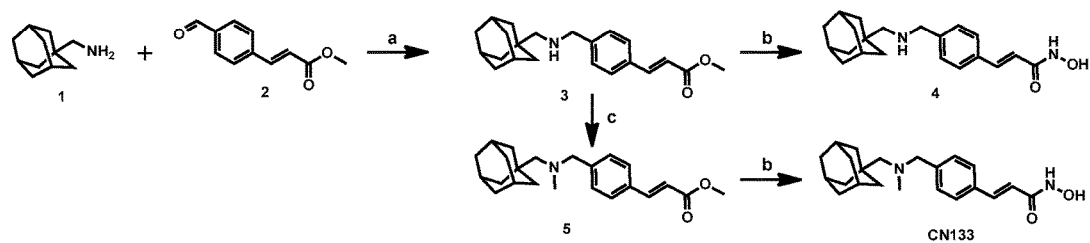
FIG. 2 shows a scheme for synthesizing hydroxyacrylamides suitable for use in the invention.

FIG. 2 shows an scheme for synthesizing hydroxyacrylamides suitable for use in the invention. In the scheme of FIG. 2, the reagents and conditions are: (a) $NaBH_4$, MeOH, overnight, room temperature, 75%; (b) $NH_2OH$ (aq), 1M NaOH, MeOH/THF, 0° C. to room temperature, 4 hours, 40% for 4 in FIG. 2, 42% for CN133; (c) formaldehyde, AcOH, $NaBH_4$, MeOH, room temperature, overnight, 55%.

(E)-methyl 3-(4-((((3r,5r,7r)-adamantan-1-ylmethyl)amino)methyl)phenyl)acrylate (3 in FIG. 2)

Adamantan-1-ylmethanamine (1 in FIG. 2) (1 g, 6.0 mmol) and (E)-methyl 3-(4-formylphenyl)acrylate (2 in FIG. 2) (1 g, 5.3 mmol) was dissolved in MeOH (30 mL) and the mixture was stirred at room temperature for 2 hours. Sodium borohydride (0.61 g, 16 mmol) was then added, and the suspension was stirred overnight at room temperature. The white precipitate was filtered and dried to obtain the product (3 in FIG. 2) (1.35 g, yield: 75%). $^1$H-NMR (500 MHz, $CDCl_3$): δ 7.69 (d, J=16 Hz, 1H), 7.48 (d, J=7 Hz, 2H), 7.35 (d, J=7 Hz, 2H), 6.43 (d, J=16 Hz, 1H), 3.81 (s, 2H), 3.80 (s, 3H), 2.23 (s, 3H), 1.96 (s, 3H), 1.63-1.73 (m, 6H), 1.53 (s, 6H); $^{13}$C-NMR (125 MHz, CDCl3): 167.55, 144.78, 143.81, 132.87, 128.35 (2C), 128.08 (2C), 117.10, 62.15, 54.28, 51.65, 40.85 (3C), 37.24 (3C), 33.49, 28.48 (3C). LC-MS calculated for $C_{22}H_{29}NO_2$ expected [M]: 339.2; Found [M+H]$^+$: 340.3.

(E)-3-(4-((((3r,5r,7r)-adamantan-1-ylmethyl)amino)methyl)phenyl)-N-hydroxyacrylamide (4 in FIG. 2)

To a solution of 3 (in FIG. 2) (0.5 g, 1.5 mmol) in MeOH/THF (5 mL/5 mL) at 0° C. was added $NH_2OH$ (50% aq. solution, 3 mL) followed by 1 M NaOH (2 mL). The mixture was stirred at 0° C. for 2 hours, warmed to room temperature, and stirred for 2 hours. Acidification with 1 M HCl to pH 7-8 (pH paper) resulted in product precipitation. The precipitate was filtered and dried to obtain 4 in FIG. 2 (0.2 g, 40%) as white solid. $^1$H-NMR (500 MHz, $CDCl_3$): δ 7.69 (d, J=16 Hz, 1H), 7.47 (d, J=7.5 Hz, 2H), 7.39 (d, J=7.5 Hz, 2H), 6.42 (d, J=16 Hz, 1H), 3.80 (s, 3H), 3.54 (s, 2H), 2.19 (s, 3H), 2.10 (s, 2H), 1.95 (s, 3H), 1.62-1.723 (m, 6H), 1.53 (s, 6H); $^{13}$C-NMR (125 MHz, $CDCl_3$): 164.92, 141.31, 139.69, 133.75, 128.61 (2C), 127.42 (2C), 116.88, 71.09, 61.08, 53.31, 40.41 (3C), 36.77 (3C), 32.84, 28.48 (3C). LC-MS calculated for $C_{21}H_{28}N_2O_2$ expected [M]: 340.5; Found [M+H]$^+$: 341.3.

(E)-methyl 3-(4-((((3r,5r,7r)-adamantan-1-ylmethyl)(methyl)amino)methyl)phenyl)acrylate (5 in FIG. 2)

To a solution of 3 (in FIG. 2) (0.5 g, 1.5 mmol) in MeOH (30 mL) was added formaldehyde (33% aq. solution, 2 mL) followed by acetic acid (0.1 mL). The mixture was stirred at room temperature for 2 hours. Sodium borohydride (0.61g, 16 mmol) was then added, and the suspension was stirred overnight at room temperature. The white precipitate was filtered and purified by flash chromatography in hexanes:ethyl acetate (4:1) to obtain the product 3 in FIG. 2 (0.29 g, yield: 55%) as white solid. $^1$H-NMR (500 MHz, MeOH-d4): δ 7.55 (d, J=16 Hz, 1H), 7.52 (d, J=7.5 Hz, 2H), 7.37 (d, J=7.5 Hz, 2H), 6.47 (d, J=16 Hz, 1H), 3.77 (s, 2H), 2.21 (s, 2H), 1.94 (s, 3H), 1.66-1.76 (m, 6H), 1.54-1.55 (m, 6H); $^{13}$C-NMR (125 MHz, MeOH-d4): 164.93, 141.32, 139.71, 133.76, 128.62 (2C), 127.43 (2C), 116.8901, 61.08, 53.32, 40.42 (3C), 36.78 (3C), 32.84, 28.48 (3C). LC-MS calculated for $C_{21}H_{28}N_2O_2$ expected [M]: 340.2; Found [M+H]$^+$: 341.3.

(E)-3-(4-((((3r,5r,7r)-adamantan-1-ylmethyl)(methyl)amino)methyl)phenyl)-N-hydroxyacrylamide (CN133 in FIG. 2)

To a solution of 5 (in FIG. 2) (0.5 g, 1.4 mmol) in MeOH/THF (3 mL/3 mL) at 0° C. was added $NH_2OH$ (50% aq. solution, 3 mL) followed by 1 M NaOH (2 mL). The mixture was stirred at 0° C. for 2 hours, warmed to room temperature, and stirred for 2 hours. Acidification with 1 M HCl to pH 7-8 (pH paper) resulted in product precipitation. The precipitate was filtered and dried to obtain CN133 in FIG. 2 (0.21 g, 42%) as white solid. $^1$H-NMR (500 MHz, DMSO-d6): δ 7.49 (d, J=7.5 Hz, 2H), 7.42 (d, J=16 Hz, 1H), 7.33 (d, J=7.5 Hz, 2H), 6.45 (d, J=16 Hz, 1H), 3.48 (s, 2H), 2.11 (s, 3H), 2.06 (s, 2H), 1.89 (s, 3H), 1.55-1.65 (m, 6H), 1.46 (s, 6H); δ 13C-NMR (125 MHz, DMSO-d6): 163.15, 142.00, 138.43, 139.91, 129.36 (2C), 127.77 (2C), 119.06, 70.12, 64.57, 45.71, 41.01 (3C), 37.21 (3C), 35.27, 28.33 (3C). LC-MS calculated for $C_{22}H_{30}N_2O_2$ expected [M]: 354.2; Found [M+H]$^+$: 355.3.

HDAC Inhibition Assay

All histone deacetylases were purchased from BPS Bioscience. The substrates, Broad Substrate A, and Broad Substrate B, were synthesized and are now available commercially through Perkin Elmer. All the other reagents were purchased from Sigma-Aldrich. Caliper EZ reader II system was used to collect all data. HDAC inhibition assays: Compounds were tested in duplicate in a 12-point dose curve with 3-fold serial dilution starting from 33.33 μM. Purified HDACs were incubated with 2 μM carboxyfluorescein (FAM)-labeled acetylated or trifluoroacetylated peptide substrate (Broad Substrate A and B respectively) and test compound for 60 minutes at room temperature, in HDAC assay buffer that contained 50 mM HEPES (pH 7.4), 100 mM KCl, 0.01% BSA and 0.001% Tween-20. Reactions were terminated by the addition of the known pan HDAC inhibitor LBH-589 (panobinostat) with a final concentration of 1.5 μM. Substrate and product were separated electrophoretically and fluorescence intensity in the substrate and product peaks was determined and analyzed by Labchip EZ Reader. The reactions were performed in duplicate for each sample. $IC_{50}$ values were automatically calculated by Origin 8 using 4 Parameter Logistic Model. The percent inhibition was plotted against the compound concentration, and the $IC_{50}$ value was determined from the logistic dose-response curve fitting by Origin 8.0 software.

Figure 3:
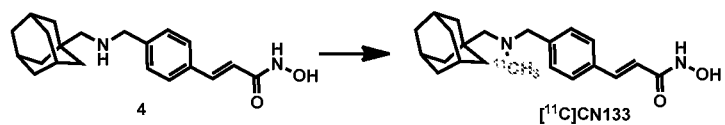
FIG. 3 shows a scheme for synthesizing an example radioisotope labeled hydroxyacrylamide, [$^{11}$C]CN133, suitable for use in the invention.

Radiosynthesis of [$^{11}$C]CN133 (FIG. 3)

$^{11}CO_2$ was obtained via the $^{14}$N(p, α)$^{11}$C reaction on nitrogen with 2.5% oxygen, with 11 MeV protons (Siemens Eclipse cyclotron), and trapped on molecular sieves in a TRACERlab FX-Mel synthesizer (General Electric). $^{11}CH_4$ was obtained by the reduction of $^{11}CO_2$ in the presence of hydrogen at 350° C. and passed through an oven containing $I_2$ to produce $^{11}CH_3I$ via a radical reaction. $^{11}CH_3I$ was trapped in a TRACERlab FX-M synthesizer reactor (General Electric) preloaded with a solution of precursor (4 in FIG. 3) (1.0 mg) in dry DMSO (300 µL). The solution was stirred at 100° C. for 4 minutes and water (1.2 mL) was added. The reaction mixture was purified by reverse phase semi-preparative HPLC (Phenomenex Luna 5u C8(2), 250 mm×10 mm, 5 µm, 5.0 mL/min, 40% $H_2O$+ammonium acetate (0.1 M)/60% $CH_3CN$) and the desired fraction was collected. The final product was reformulated by loading onto a solid-phase exchange (SPE) C-18 cartridge, rinsing with 1M NaOH aq (5 mL), eluting with EtOH (1 mL), and diluting with 50 µL acetic acid in saline (0.9%, 9 mL). The chemical and radiochemical purity of the final product was tested by analytical HPLC (Agilent Eclipse XDB-C18, 150 mm×4.6 mm). The identity of the product was confirmed by analytical HPLC with additional co-injection of CN133 reference standard. The average time required for the synthesis from end of cyclotron bombardment to end of synthesis was 35 minutes. The average radiochemical yield was 3-5% (non-decay corrected to trapped [$^{11}C$]$CH_3I$; n=3). Chemical and radiochemical purities were ≥95% with a specific activity 1.0±0.2 Ci/µmol (EOB).

Specific Activity of [$^{11}C$]CN133

Figure 4:
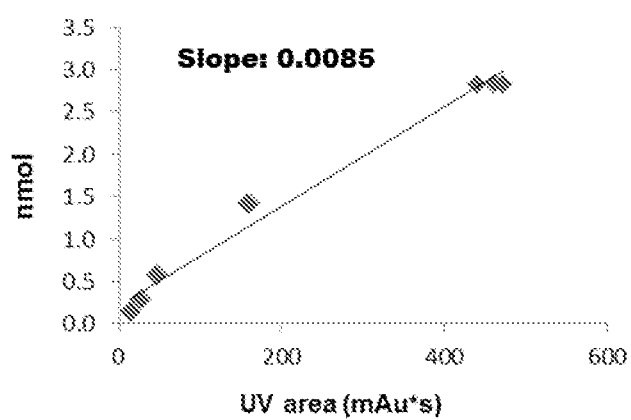
FIG. 4 shows a mass/UV calibration curve for [$^{11}$C]CN133 of FIG. 3.

Specific radioactivity (SA) of [$^{11}C$]CN133 was calculated from an analytical HPLC sample of 100 µL. A calibration curve of known mass quantity versus HPLC peak area (254 nm) was used to calculate the mass concentration of the 100 µL. SA was determined using the mass concentration value determined for the formulated [$^{11}C$]CN133 solution, volume, and measured radioactivity. The identity of the mass peak assigned to [$^{11}C$]CN133 was supported by a replicated injection where [$^{11}C$]CN133 was treated with nonradioactive CN133. The calibration curve used is shown in FIG. 4 wherein the mass/UV calibration curve has five concentrations (0.5, 1.0, 2.0, 5.0, 10.0 µM) of standard CN133 were imaged and 100 µL (n=3) of each concentration were injected into analytical HPLC column (UV: 254 nM) (Agilent; Gemini C18, 250×4.6 mm).

Log D Determination

An aliquot (~50 µL) of the formulated radiotracer was added to a test tube containing 2.5 mL of octanol and 2.5 mL of phosphate buffer solution (pH 7.4). The test tube was mixed by vortex for 2 minutes and then centrifuged for 2 minutes to fully separate the aqueous and organic phase. A sample taken from the octanol layer (0.1 mL) and the aqueous layer (1.0 mL) was saved for radioactivity measurement. An additional aliquot of the octanol layer (2.0 mL) was carefully transferred to a new test tube containing 0.5 mL of octanol and 2.5 mL of phosphate buffer solution (pH 7.4). The previous procedure (vortex mixing, centrifugation, sampling, and transfer to the next test tube) was repeated until six sets of aliquot samples had been prepared. The radioactivity of each sample was measured in a well counter (Perkin-Elmer, Waltham, Mass.). The log D of each set of samples was derived by the following equation: log D=log (decay-corrected radioactivity in octanol sample×10/decay-corrected radioactivity in phosphate buffer sample).

Plasma Protein Binding Assay

An aliquot of radiotracer in saline (10 µL) was added to a sample of baboon plasma (0.8 mL, pooled from two separate animals). The mixture was gently mixed by repeated inversion and incubated for 10 minutes at room temperature. Following incubation a small sample (20 µL) was removed to determine the total radioactivity in the plasma sample ($A_T$; $A_T=A_{bound}+A_{unbound}$). An additional 0.2 mL of the plasma sample was placed in the upper compartment of a Centrifree tube (Amicon, Inc., Beverly, Mass., USA) and then centrifuged for 10 minutes. The upper part of the Centrifree tube was discarded, and an aliquot (20 µL) from the bottom part of the tube was removed to determine the amount of radioactivity that passed through the membrane ($A_{unbound}$). Plasma protein binding was derived by the following equation: % unbound=$A_{unbound}$×100/$A_T$.

Rodent PET/CT Acquisition and Post Processing

Male Sprague-Dawley rats were utilized in pairs, anesthetized with inhalational isoflurane (Forane) at 3% in a carrier of 2 L/min medical oxygen and maintained at 2% isoflurane for the duration of the scan. The rats were arranged head-to-head in a Triumph Trimodality PET/CT/SPECT scanner (Gamma Medica, Northridge, Calif., USA). Rats were injected standard references or vehicle via a lateral tail vein catheterization at the start of PET acquisition. Dynamic PET acquisition lasted for 60 minutes and was followed by computed tomography (CT) for anatomic coregistration. PET data were reconstructed using a 3D-MLEM method resulting in a full width at half-maximum resolution of 1 mm. Reconstructed images were exported from the scanner in DICOM format along with an anatomic CT for rodent studies. These files were imported to PMOD (PMOD Technologies, Ltd.) and manually coregistered using six degrees of freedom.

Rodent PET/CT Image Analysis

Volumes of interest (VOIs) were drawn manually as spheres in brain regions guided by high resolution CT structural images and summed PET data, with a radius no less than 1 mm to minimize partial volume effects. Time-activity curves (TACs) were exported in terms of decay corrected activity per unit volume at specified time points with gradually increasing intervals. The TACs were expressed as percent injected dose per unit volume for analysis.

Figure 5:
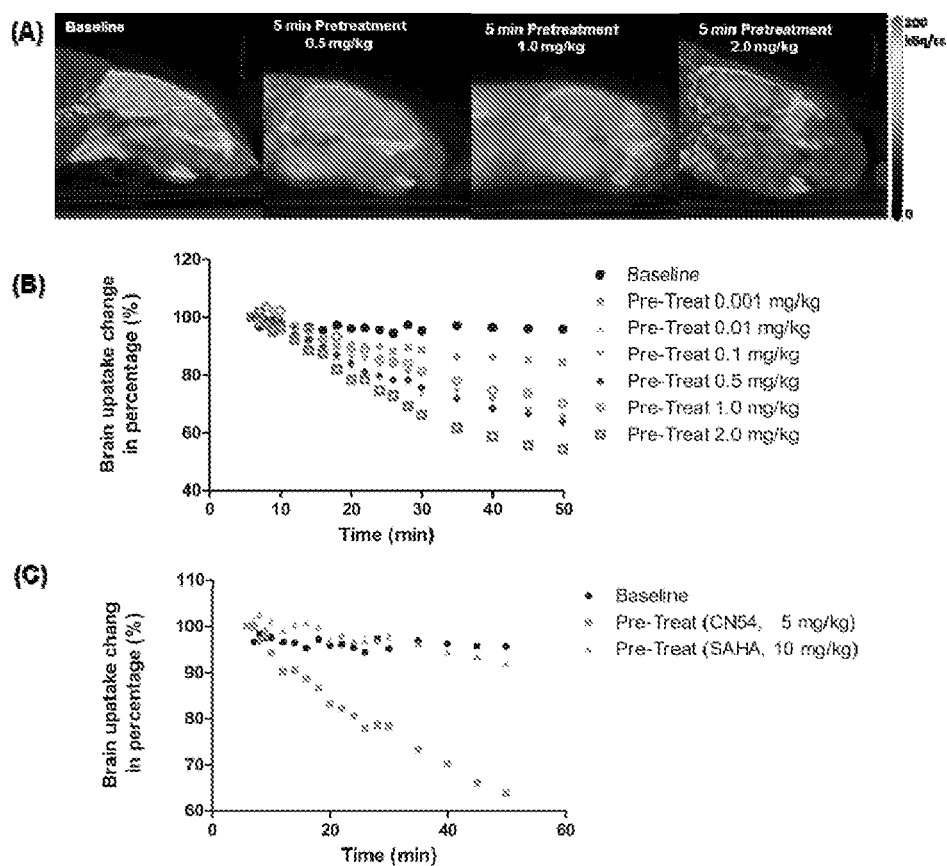
FIG. 5 shows images and brain uptake graphs from PET imaging of a rodent using [$^{11}$C]CN133 of FIG. 3.

FIG. 5 shows the rodent imaging experiments with [$^{11}C$]CN133. In (A), there is shown summed PET images (1-60 minutes) following injection of [$^{11}C$]CN133. In (B), there is shown the brain uptake changes in whole-brain generated from rodents PET imaging data after 5-minutes pretreatment of vehicle, 0.001 mg/kg, 0.01 mg/kg, 0.1 mg/kg, 0.5 mg/kg, 1.0 mg/kg and 2.0 mg/kg of CN133. In (C), there is shown the brain uptake changes in whole-brain after 5-minute pretreatment of vehicle, CN54 and SAHA.

Figure 6:
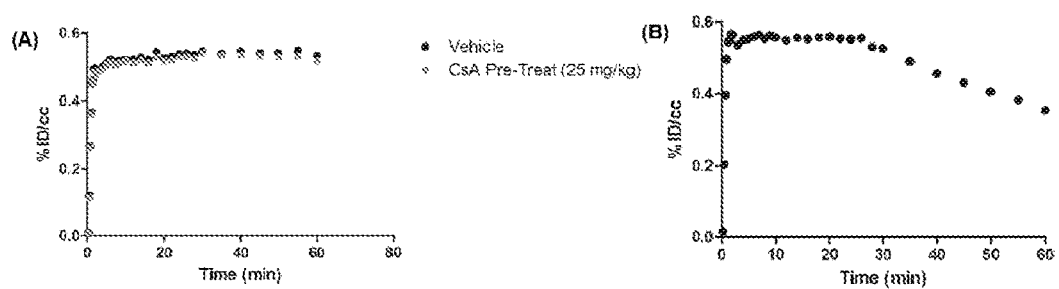
FIG. 6 shows the results of rodent imaging experiments with [$^{11}$C]CN133 of FIG. 3. In (A), there is shown a pretreatment with cyclosporin A (CsA). In (B), there is shown the administration of the unlabeled hydroxyacrylamide of FIG. 3 after 20 minutes of imaging with [$^{11}$C]CN133 of FIG. 3.

FIG. 6 shows further rodent imaging experiments with [$^{11}C$]CN133. In (A), there is shown rodent imaging experiments with 30-minute pretreatment of CsA (25 mg/kg). In (B), there is shown the administration of CN133 (1.0 mg/kg) after 20 minutes imaging with [$^{11}C$]CN133. FIG. 6(A) provides evidence that CN133 is not a Pgp inhibitor. FIG. 6(B) provides evidence that CN133 is a reversible inhibitor.

Figure 7:
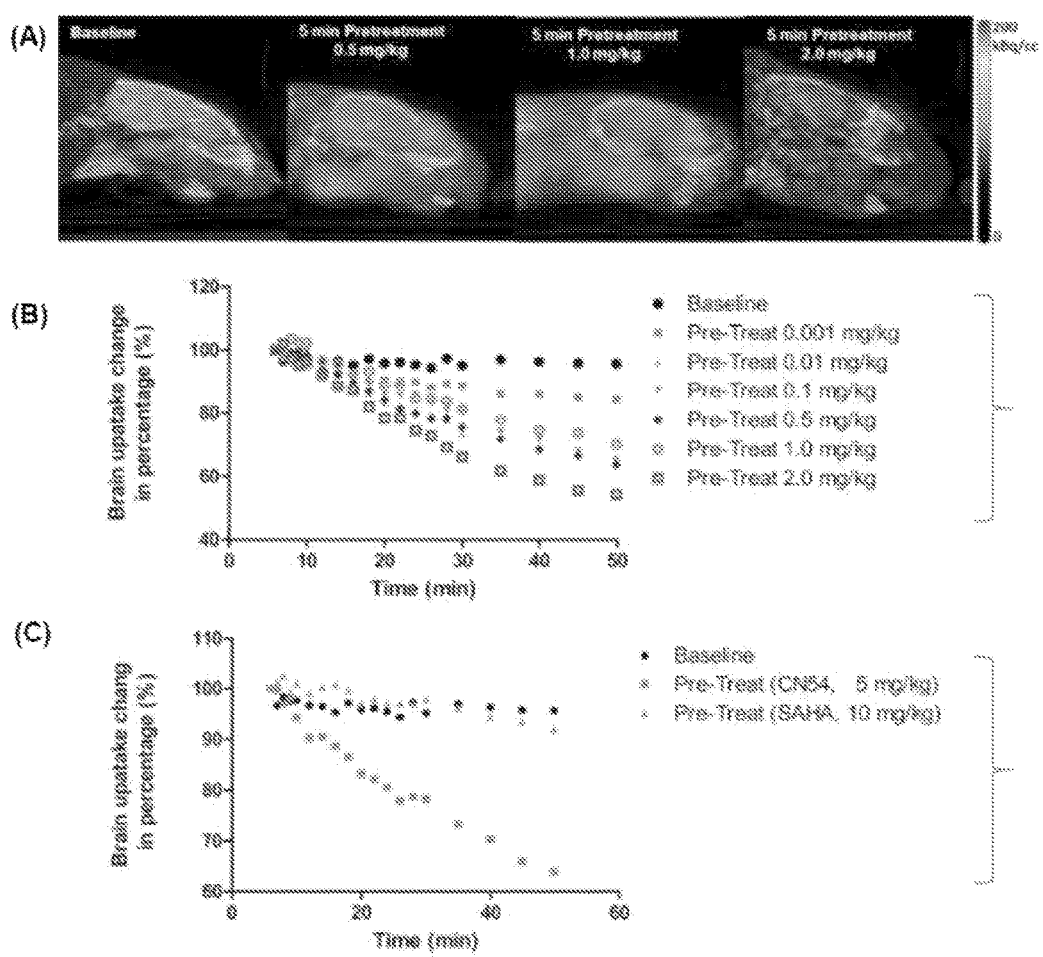
FIG. 7 shows rodent imaging experiments with [$^{11}$C]CN133 of FIG. 3. In (A), there is shown summed PET images following injection of [$^{11}$C]CN133 of FIG. 3. In (B), there is shown the brain uptake changes in whole-brain generated from rodents PET imaging data after 5-minutes of pretreatment of the unlabeled hydroxyacrylamide of FIG. 3. In (C), there is shown the brain uptake changes in whole-brain after 5-minute pretreatment of vehicle, CN54 (shown below) and suberanilohydroxamic acid (SAHA).

FIG. 7 shows rodent imaging experiments with [$^{11}C$]CN133. In (A), there is shown summed PET images (1-60 minutes) following injection of [$^{11}$C]CN133. In (B), there is shown the brain uptake changes in whole-brain generated from rodents PET imaging data after 5-minutes of pretreatment of vehicle, 0.001 mg/kg, 0.01 mg/kg, 0.1 mg/kg, 0.5 mg/kg, 1.0 mg/kg and 2.0 mg/kg of CN133. FIG. 7(B) shows dose response in the brain (self saturation). In (C), there is shown the brain uptake changes in whole-brain after 5-minute pretreatment of vehicle, CN54 and SAHA. FIG. 7(C) shows CN133 blocked by the brain penetrant HDACi (CN54) and not by SAHA, which has an extremely low blood-brain barrier (BBB) penetration.

Figure 11:
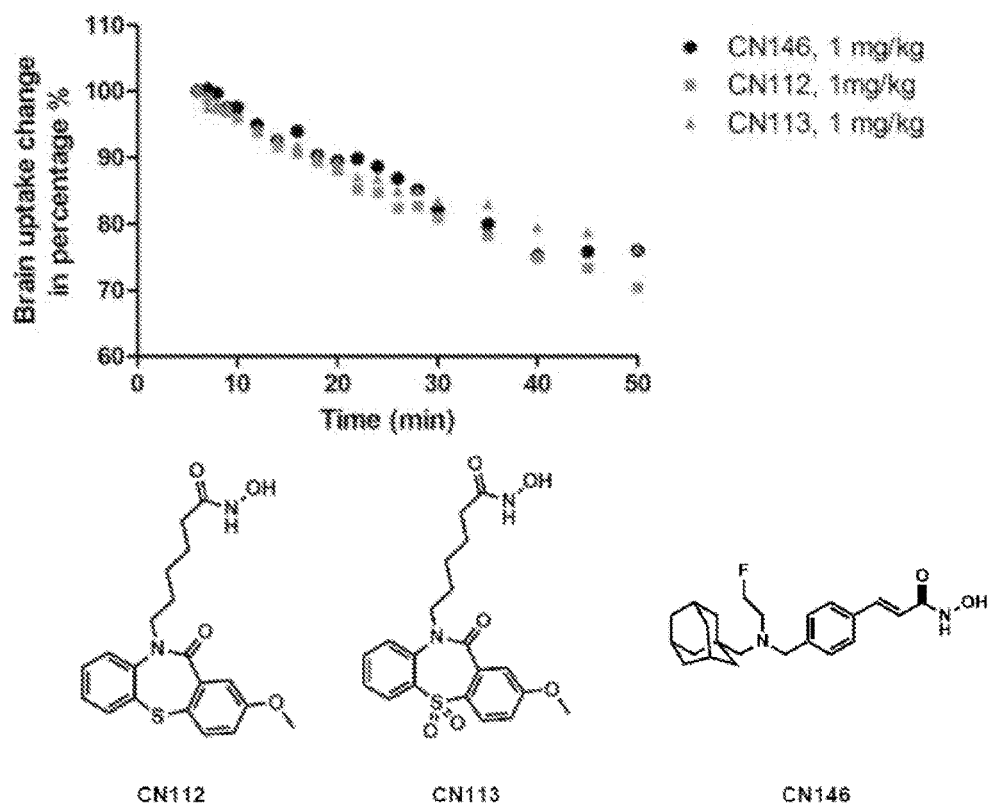
FIG. 11 shows the brain uptake changes in rodent whole-brain with administration of [$^{11}$C]CN133 of FIG. 3 after 5-minute pretreatment of CN112, CN113 and CN146 at 1 mg/kg.

FIG. 11 shows rodent imaging experiments with [$^{11}$C] CN133 after 5-minute pretreatment of CN112, CN113 and CN146 at 1 mg/kg.

Figure 12:
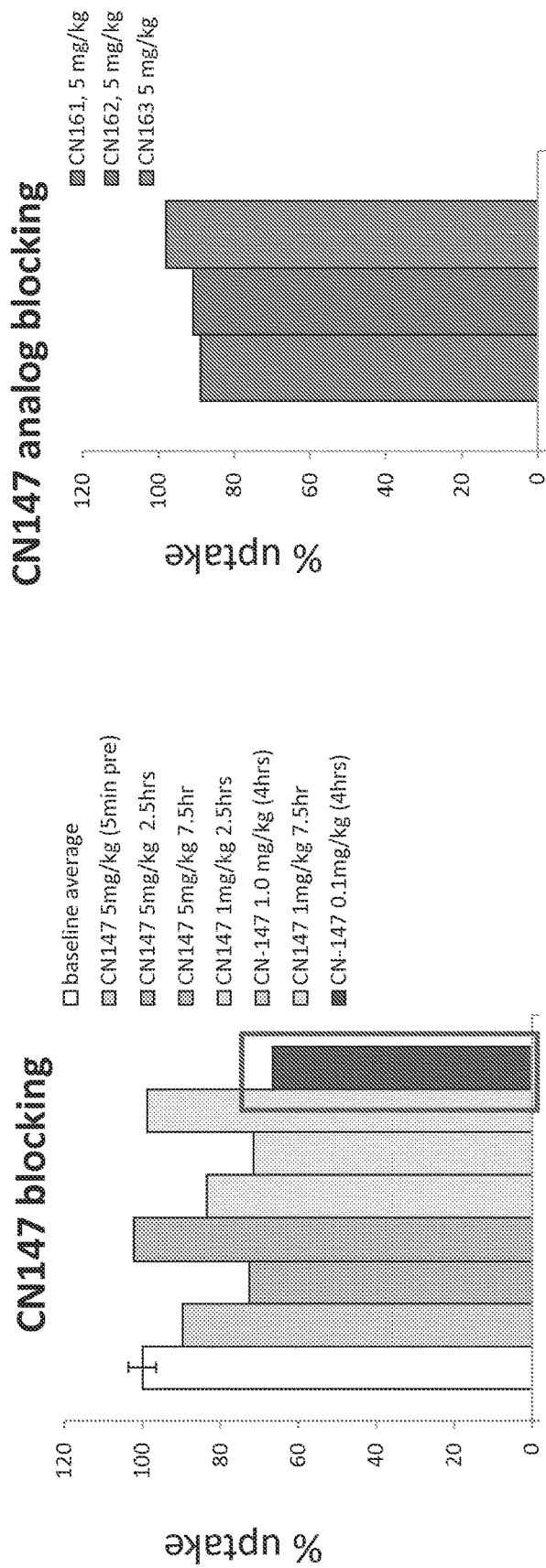
FIG. 12 shows rodent imaging experiments with [$^{11}$C]CN133 of FIG. 3 after pretreatment with the structurally distinct HDAC inhibitor tool compounds and putative therapeutic leads CN147, CN161, CN162, or CN163 (shown below). The graph legends top to bottom correspond left to right in the bars in the graphs.

FIG. 12 shows rodent imaging experiments with [$^{11}$C] CN133 after pretreatment of CN147, CN161, CN162, or CN163 (shown above). CN147 analogs demonstrate blocked binding of [$^{11}$C]CN133 in rat brain by in vivo PET imaging as measured by % uptake of [$^{11}$C]CN133 in whole rat brain. The results indicate that 0.1 mg/kg CN147 is sufficient to robustly occupy HDAC targets in brain. Results indicate that CN147 analogs CN161 and CN162 also occupy HDAC targets in brain (5 mg/kg, administered i.p., 2.5 hours prior to radiotracer).

Baboon PET/MR Acquisition and Post Processing

A female *Papio Anubis* baboon, deprived of food for 12 hours prior to the study, was administered intramuscular ketamine (10 mg/kg) and intubated. For maintenance of anesthesia throughout the study, the baboon was provided 1%-4% isoflurane (Forane) in a mixture of medical oxygen and nitrogen. The baboon was catheterized antecubitally for radiotracer injection and a radial arterial line was placed for metabolite analysis. MR-PET images were acquired in a BiographmMR scanner (Siemens, Munich, Germany), and PET compatible 8-channel coil arrays for non-human primate brain imaging with a PET resolution of 5 mm and field of view of 59.4 cm and 25.8 cm (transaxial and axial, respectively). Dynamic PET image acquisition was initiated followed by administration of the radiotracer in a homogenous solution of 10% ethanol and 90% isotonic saline. An MEMPRAGE sequence began after 30 minutes of the baseline scan for anatomic coregistration. To characterize the specific binding of [$^{11}$C]CN133, a second imaging experiment was carried out in which unlabeled CN133 was co-administered intravenously at the start of acquisition. Both scans were carried out in the same animal on the same day, separated by 2.5 hours. In both scans, 4-5 mCi of [$^{11}$C] CN133 was administered to the baboon. Dynamic data from the PET scans were recorded in list mode and corrected for attenuation. Baboon data were reconstructed using a 3D-OSEM method resulting in a full width at half-maximum resolution of 4 mm.

Baboon PET/MR Image Analysis

Volumes of interest (VOIs) were drawn manually as spheres in brain regions guided by high resolution MR structural images and summed PET data, with a radius no less than 4 mm. A common VOI mask was applied to both baboon scans. Time-activity curves (TACs) were exported in terms of decay corrected activity per unit volume at specified time points with gradually increasing intervals. The TACs were expressed as percent injected dose per unit volume for analysis.

Plasma And Metabolite Analysis

Arterial samples collected during imaging from the baboon were centrifuged to obtain plasma, which was then removed and placed in an automated gamma counter that was calibrated to the PET scanner. Metabolite analysis was conducted on a custom automated robot fitted with Phenomenex SPE Strata-X 500 mg solid phase extraction cartridges that were primed with ethanol (2 mL) and deionized water (20 mL). Protein precipitation was achieved by addition of plasma (300 μL) to acetonitrile (300 μL), which was centrifuged for 1 minute to obtain protein-free plasma (PFP). 300 μL of PFP/acetonitrile solution was diluted into deionized water (3 mL), loaded onto the C18 cartridge, and removed of polar metabolites with 100% water. Next, a series of extractions were performed using water and acetonitrile in quantities: 95:5, 90:10, 85:15, 80:20, 70:30, 60:40, 30:70 and 100% acetonitrile at a volume of 4 mL. A control experiment was performed before metabolite analysis to determine the retention of the parent compound by injection of a small amount of [$^{11}$C]CN133 onto a test series of extraction cartridges. Each sample was counted in a WIZARD2 Automatic Gamma Counter to determine the presence of radiolabeled metabolites.

Baboon PET/MR Image Analysis

Figure 13:
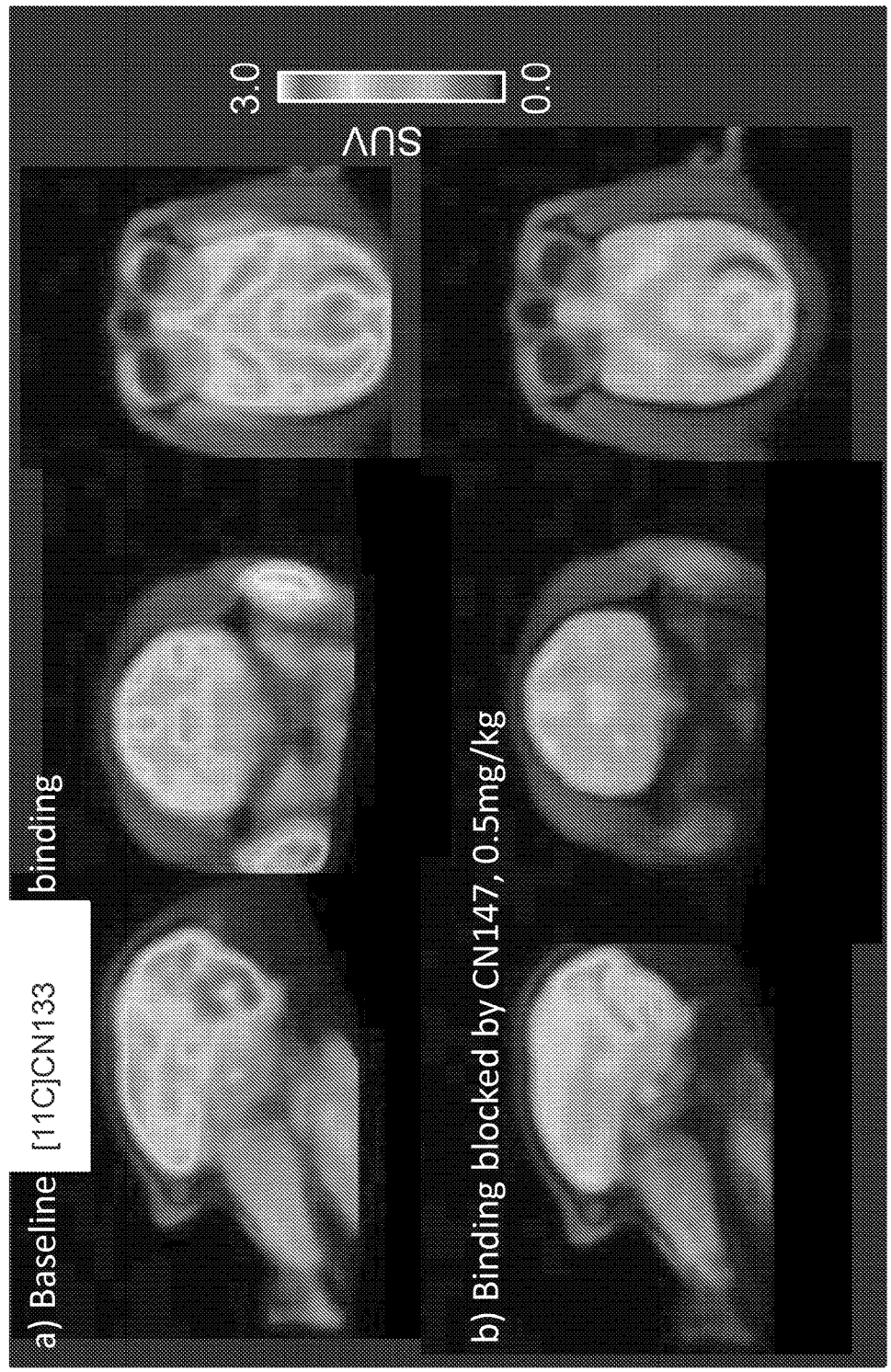
FIG. 13 shows that the prototypical HDAC inhibitor tool compound/therapeutic lead CN147 (shown below) demonstrates blocked binding of [$^{11}$C]CN133 of FIG. 3 in non-human primate in vivo imaging. The color scale bar illustrates standardized uptake values (SUV).

FIG. 13 shows that CN147 demonstrates blocked binding in Non-Human Primate (NHP) in vivo imaging. Standardized uptake value (SUV) maps demonstrate that compared to baseline (a) intravenous treatment with CN147 (0.5 mg/kg) blocks radiotracer uptake in baboon brain (b) [SUV maps, summed 30-80 min].

CN147 blocks ~40% of [$^{11}$C]CN133 binding in NHP whole brain and in cerebellum. Plasma-normalized data were evaluated by volume of interest analysis (VOI) at the whole brain level and at level of the cerebellum. VOI data were then applied to distribution volume (VT) data analysis by two graphical methods using PMOD software, tabulated in Tables A and B below. Logan Plot and Ichese MAI methods were clarified from previous NHP imaging analyses to provide an accurate VT estimate (+/− standard error) from data beginning 35 min after injection of radiotracer (t*=35 min) until the end of the scan (t=80min). Additional regions were analyzed and Vt quantified for radiotracer uptake at baseline and after intravenous pretreatment with unlabeled CN133 (FIG. 14B) and demonstrate differential tracer uptake throughout the non-human primate brain, indicative of differential HDAC target expression/ binding availability.

TABLE A

| Whole Brain VOI | Baseline | CN147 blocked | % Difference |
|---|---|---|---|
| VT (Logan Plot) | 14.46 ± 3.83 | 8.85 ± 3.06 | 38.80 |
| VT (Ichese MAI) | 14.65 ± 8.48 | 8.92 ± 9.26 | 39.11 |

TABLE B

| Cerebellum VOI | Baseline | CN147 blocked | % Difference |
|---|---|---|---|
| VT (Logan Plot) | 19.28 ± 3.18 | 11.59 ± 3.37 | 39.89 |
| VT (Ichese MAI) | 19.45 ± 7.5 | 11.68 ± 8.42 | 39.95 |

Human PET/MR Acquisition and Post Processing

PET-MR imaging of human brain: Simultaneous PET and MRI data were acquired on an integrated MR-PET scanner allowing us to further improve the performance of each of the separate instruments by using the information obtained from the other modality. This study used the Biography mMR (Siemens, Munich, Germany), which was recently approved by the FDA and applied the imaging probe [$^{11}$C]CN133, also recently approved for imaging in humans by the FDA. Dynamic PET image acquisition (90 min) was initiated followed by administration of the radiotracer [$^{11}$C]CN133, in a homogenous solution of 10% ethanol and 90% isotonic saline. A high-resolution multiplanar magnetization prepared rapidly acquired gradientecho (MPRAGE) structural scan began after 30 min of the baseline scan for anatomic coregistration (1 mm$^3$ isotropic voxels; 176 interleaved slices; field of view (FoV)=256 mm; matrix size: 256×256; slice thickness=1 mm; 0.5 mm inter-slice gap; repetition time (TR)=2530 ms; echo time (TE)=3.44 ms; flip angle=7°). In each scan, 3-5 mCi of [$^{11}$C]CN133 was administered to human. Dynamic data from the PET scans were recorded in list mode and corrected for attenuation. Imaging data was reconstructed using a 3D-OSEM method resulting in a full width at half-maximum resolution of 4 mm.

Human PET/MR Image Analysis

PET images were corrected for motion using a recently developed MR-based method or a frame-to-frame registration process with a mutual information cost function. The motion corrected volumes were implicitly co-registered to the anatomic MRI scans and the dynamic PET data summed from scan timepoints 40 min-90 min to illustrate accumulated radioactivity (14A). All data were evaluated using metabolite-corrected arterial plasma activity as input function, as described for NHP.

Dynamic data provide regional time-activity curves. Kinetic modeling will be performed using PMOD 3.3 (PMOD Technologies Ltd., Zurich, Switzerland). The volumes of interest (VOIs) will be defined according to a human brain atlas. Common VOIs will be applied to all scans. As a non-limiting example of regions targeted for analysis, time-activity curves (TACs) will be extracted from the thalamus, caudate, putamen, nucleus accumbens (NAc), amygdala, hippocampus, cerebellum, primary motor cortex (M1), primary visual cortex (V1), dorsal lateral prefrontal cortex (DLPFC), orbital frontal cortex (OFC), supplementary motor area (SMA), and posterior cingulate cortex (PCC) VOIs for analysis.

Results

Design and Synthesis of PET Imaging Agents with Brain Permeability

HDAC inhibitors comprise diverse structural classes including hydroxamic acids, natural cyclic peptides, short-chain fatty acids as well as aminoanilines and ketones. All classes of HDAC inhibitors contain three key structural elements to their pharmacophore: (i) a zinc-binding group which coordinates the zinc ion, (ii) a capping group and (iii) a linker domain. The brain uptake of most HDAC inhibitors is limited as reported; hence, to increase the brain permeability, the structure should be modified with "BBB carriers" to keep low molecular weight of the inhibitors. An adamantyl group is one of our example carriers to increase the brain uptake, so we designed a cinnamic-based HDAC inhibitor containing the adamantyl group (see FIG. 2). Briefly, the compounds are achieved through the amine-reduction reaction, and then convert the ester into hydroxamic acid in the presence of hydroxylamine and sodium hydroxide. The synthesis of [$^{11}$C]CN133 was accomplished using its precursor in DMSO with [$^{11}$C]methyl iodine ([$^{11}$C]CH$_3$I) as outlined in FIG. 3.

Physicochemical Properties Of CN133

The in vitro inhibitory activities of CN133 were measured for each HDAC isoform HDAC1 through HDAC9 (see Table 1 below). The IC$_{50}$ value for SAHA (Vorinostat, suberanilohydroxamic acid, a histone deacetylase inhibitor) was measured in parallel as a reference. The CN133 showed low nanomolar IC$_{50}$ towards class-I HDAC isoforms (HDAC1-3) as well as toward class-II HDAC isoform (HDAC6), which is greater than 100-fold selectivity over each of the other HDAC isoforms. CN133 exhibits higher binding affinity towards HDAC1, HDAC 2 and HDAC 3 in vitro compared with pan-HDAC inhibitors, SAHA. The partition coefficient (Log D) and plasma protein binding (PPB) were also measured with [$^{11}$C]CN133 in vitro. The Log D is 2.03, in the preferred range for brain penetration. PPB shows 1.4% in baboon plasma and 5.5% in human plasma.

TABLE 1

| | IC$_{50}$ (nM) | | | | | | | | |
|---|---|---|---|---|---|---|---|---|---|
| | HDAC1 | HDAC2 | HDAC3 | HDAC4 | HDAC5 | HDAC6 | HDAC7 | HDAC8 | HDAC9 |
| CN133 | 0.3 | 0.8 | 0.6 | 1970 | 352 | 4.1 | >20000 | >15000 | >15000 |
| SAHA | 4.0 | 11 | 3.0 | >30000 | 8750 | 2.0 | >30000 | 1020 | >30000 |

Physicochemical Properties of Other Compounds

The in vitro inhibitory activities of other compounds described herein were measured for each HDAC isoform HDAC1 through HDAC9 (see Table 2 below). The IC$_{50}$ value for SAHA (Vorinostat, suberanilohydroxamic acid, a histone deacetylase inhibitor) was measured in parallel as a reference.

TABLE 2

| Compounds | IC50 (nM) HDAC1 | IC50 (nM) HDAC2 | IC50 (nM) HDAC3 | IC50 (nM) HDAC4 | IC50 (nM) HDAC5 | IC50 (nM) HDAC6 | IC50 (nM) HDAC7 | IC50 (nM) HDAC8 | IC50 (nM) HDAC9 |
|---|---|---|---|---|---|---|---|---|---|
| SAHA | 4.0 | 11.0 | 3.0 | >30000 | 8750.0 | 2.0 | >30000 | 1020.0 | >30000 |
| CN51 | 106.5 | 477.2 | 84.5 | NA | NA | NA | NA | NA | NA |
| CN52 | 7.3 | 20.7 | 4.3 | NA | NA | NA | NA | NA | NA |
| CN53 | 6.1 | 11.9 | 5.7 | NA | NA | NA | NA | NA | NA |
| CN54 | 56.1 | 53.7 | 7.1 | NA | NA | NA | NA | NA | NA |
| CN56 | 270.0 | 160.0 | 97.8 | NA | NA | NA | NA | NA | NA |
| CN86 | 133.0 | 470.0 | 151.0 | >10000 | >10000 | 21.7 | >20000 | 725.0 | >50000 |
| CN87 | 301.0 | 833.0 | 238.0 | >70000 | >10000 | 23.2 | >70000 | 2574.0 | >70000 |
| CN88 | 17.8 | 52.9 | 13.7 | 3831.0 | 7951.0 | 4.1 | 2017.0 | 925.0 | >10000 |
| CN89 | 5.0 | 32.0 | 3.4 | 500.0 | >10000 | 5.0 | >30000 | 150.0 | >10000 |
| CN101 | 4.7 | 18.0 | 1.9 | >10000 | >10000 | 8.4 | >40000 | 2372.0 | >50000 |
| CN107 | 0.2 | 1.2 | 0.4 | 655.0 | 99.0 | 1.6 | 2044.0 | 1044.0 | 4849.0 |
| CN110 | >30000 | 1740.0 | >50000 | NA | >70000 | 7390.0 | >70000 | 18.3 | >70000 |
| CN112 | 1.2 | 4.0 | 1.1 | >10000 | >20000 | 2.3 | 934.0 | >70000 | 1470.0 |
| CN113 | 0.8 | 2.0 | 1.3 | 9450.0 | 3850.0 | 1.2 | 9650.0 | 2840.0 | >20000 |
| CN132 | 0.95 | 7.8 | 1.2 | NA | NA | 1.7 | >20000 | >10000 | >10000 |
| CN133 | 0.3 | 0.8 | 0.6 | 1970.0 | 352.0 | 4.1 | >20000 | >15000 | >15000 |
| CN139 | 24.0 | NA | 32.7 | 2534.0 | 244.0 | 16.5 | >40000 | 2231.0 | >20000 |
| CN141 | 55.8 | NA | 97.9 | 389.0 | 207.0 | 14.4 | 5512.0 | 2400.0 | >10000 |
| CN143 | 1.8 | NA | 4.3 | 927.0 | 196.0 | 9.7 | >20000 | 9598.0 | >10000 |
| CN145 | >50000 | NA | 9239.0 | NA | >70000 | 6818.0 | NA | NA | NA |
| CN146 | 221.0 | NA | 470.0 | >10000 | 5354.0 | 308.0 | >30000 | >30000 | >40000 |
| CN148 | 0.78 | 6.4 | 0.5 | >70000 | 4308 | 9.5 | >50000 | 4900 | >50000 |
| CN149 | 0.78 | 7.0 | 0.76 | 20312 | 4747 | 11.7 | >50000 | >50000 | >50000 |
| CN165 | 96.7 | 307 | 143 | NA | NA | 2.13 | NA | 493 | NA |
| CN166 | 1.64 | 14.2 | 0.54 | NA | NA | 11.7 | NA | 725 | NA |
| CN167 | 5.43 | 40 | 4.83 | NA | NA | 18.7 | NA | 1810 | NA |

In vivo PET-CT Imaging with [11C]CN133 on Rodents

Using PET-CT, we determined that [11C]CN133 exhibited high BBB penetration and over the scanning time (60 minutes) when administered intravenously to rats (0.9-1.1 mCi per animal), as shown in FIG. 5. The summed PET-CT images showed that the radioactivity within the skull, and we also conducted the PET imaging study with the 5 minute pretreatment of reference standards at different doses (0.001, 0.01, 0.1, 0.5, 1.0 and 2.0 mg/kg), and [11C]CN133 shows dose-dependent blocking manner according to the percentage change after administration of cold compound compared with vehicle study. We also compared the brain uptake after the treatment with cyclosporin A (CsA), a P-glycoprotein (Pgp) inhibitor, but it did not show any different between treated and vehicle rats (FIG. 6A). The [11C]CN133 uptake in the peripheral organs (such as heart wall, kidney cortex and spleen) is decreased after the treatment of unlabeled CN133. To test the specificity of [11C]CN133 to other HDAC inhibitors, we pretreated the rats with SAHA and CN54 (a brain penetrant HDAC inhibitor shown above). There is no significant change in the brain region from the SAHA treated rat and CN54 shows activity blocking in the rat brain; however, there is decreased uptake in the peripheral regions from both treated rats (FIG. 7).

To determine whether the observed binding is reversible, a rats imaging study was conducted with an i.v. administration of CN133 (FIG. 6B) given 20 minutes into a baseline scan with [11C]CN133. This caused rapid washout of radioactivity from brain regions, confirming reversibility of tracer binding to histone deacetylases.

In Vivo PET-MR Imaging with [11C]CN133 in Baboon

Figure 8:
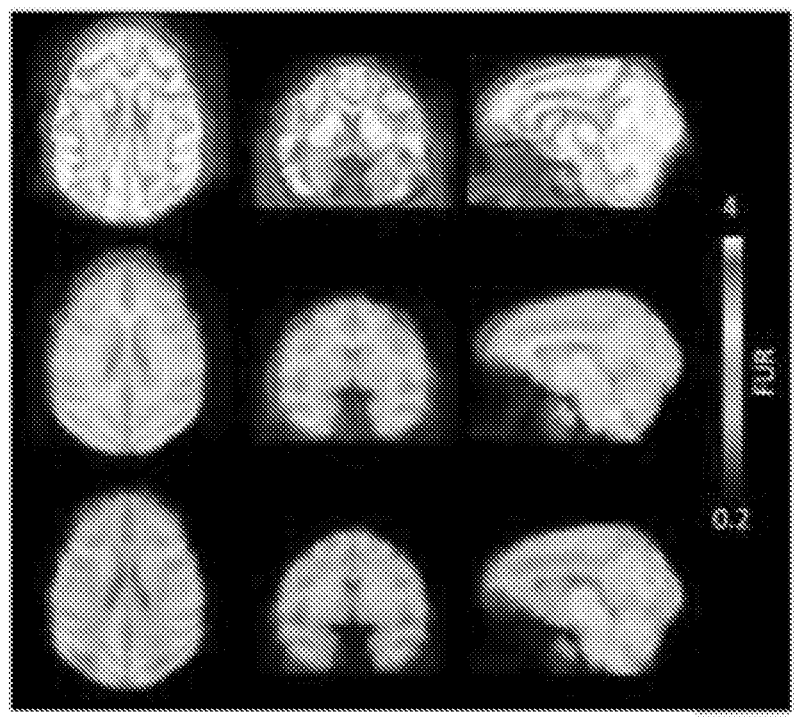
FIG. 8 shows PET-MRI images evidencing the high uptake of [$^{11}$C]CN133 of FIG. 3 in brain regions of a baboon. The top row of images is the baseline; the middle row of images is with injection of the unlabeled hydroxyacrylamide of FIG. 3 at 0.5 mg/kg; and the bottom row of images is with injection of the unlabeled hydroxyacrylamide of FIG. 3 at 1.0 mg/kg. The color scale bar illustrates fractional uptake rate (FUR).

Uptake of radioactivity into the baboon brain was seen in a baseline PET study after injection of [11C]CN133, like the results of our rodent studies. The pattern of radioactivity distribution in baboon brain is comparable with the distribution of HDACs that was found in previous experiments. The high uptake of the radiotracer was found in brain regions. Similar to the blocking results in rats, injection of unlabeled CN133 (0.01, 0.1, 0.5 and 1.0 mg/kg, intravenously) reduced the regional radioactivity uptake in the baboon brain regions with high densities of histone deacetylases (see FIG. 8). This result suggests that [11C]CN133 binds to baboon brain in the dose dependent manner, and we did not notice any significant changes in the vital signs of the baboon when either the tracer dose of [11C]CN133 or the blocking dose of CN133 was injected.

Figure 9:
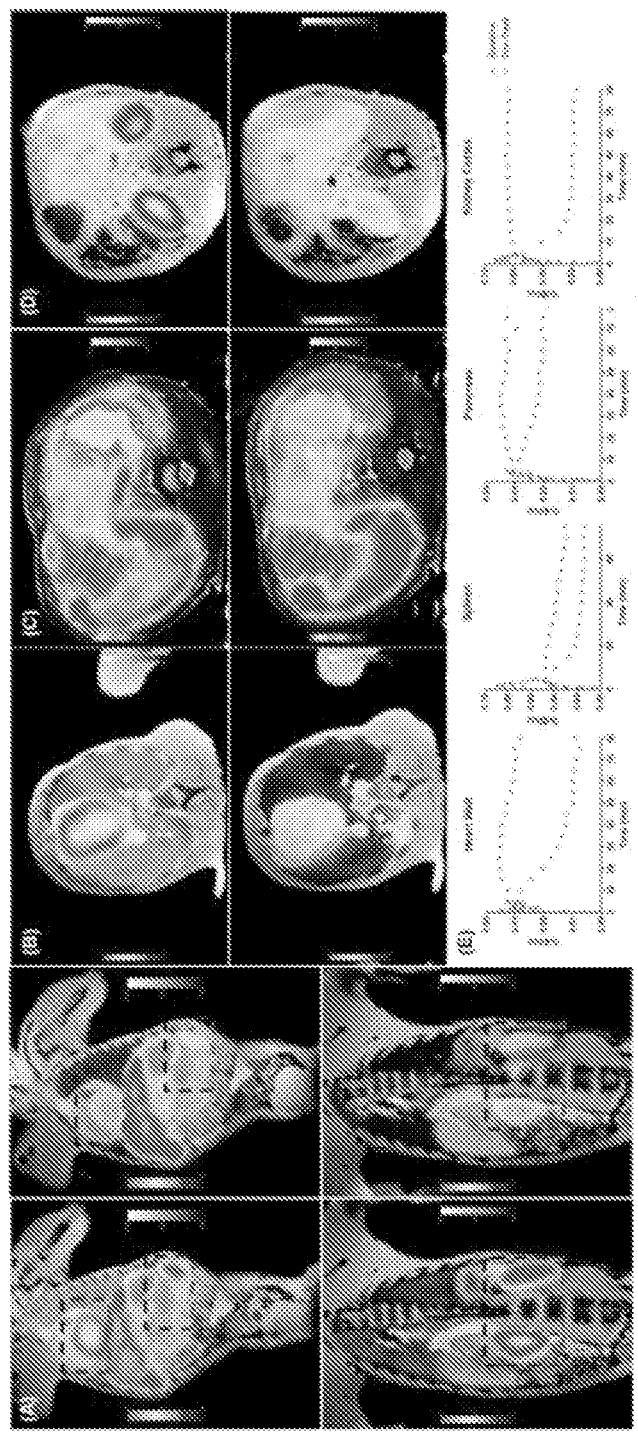
FIG. 9 shows PET-MRI imaging with administration of [$^{11}$C]CN133 of FIG. 3 for: (A) baboon body, coronal; (B) baboon heart; (C) baboon spleen and pancreas; and (D) baboon kidney.

In addition, we tested the tracer uptake and blockade in peripheral organs in baboons. [11C]CN133 shows good uptake in the organs of heart, kidney, pancreas and spleen. FIG. 9 shows [11C]CN133 PET-MRI imaging (baboon body, coronal, A). Also shown in FIG. 9 are summed PET images (20-80 minutes) superimposed with MRI images from the same baboon, following injection of radiotracers (4 mCi/baboon). Axial views are of organs-of—interest, B: heart; C, spleen and pancreas; D, kidney. The time-activity curves showed the significant blocking with 10-minute pre-treatment of unlabeled CN133 (0.5 mg/kg) in the organs, indicating the high specific binding of [11C]CN133 in these peripheral organs. The uptake of these organs is significantly decreased by the pre-treatment of unlabeled CN133, indicating that [11C]CN133 also can measure the expression of histone deacetylase in peripheral organs.

Figure 10:
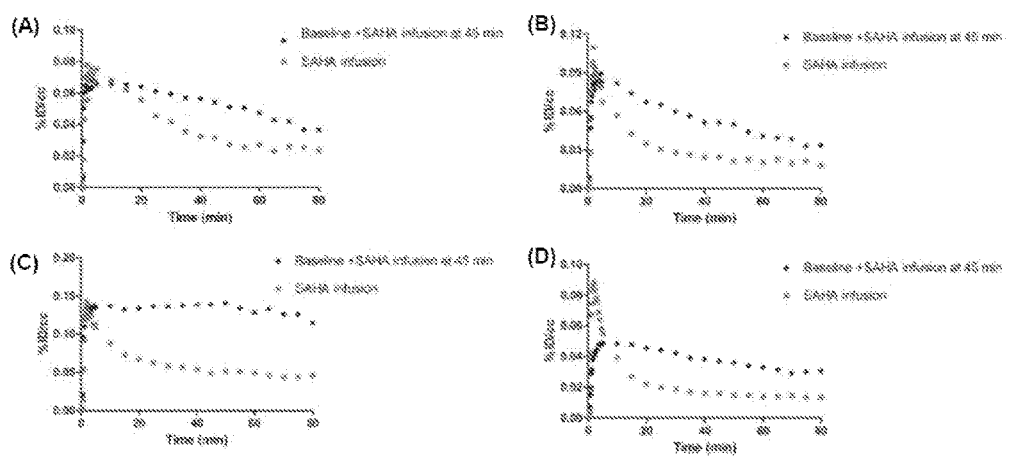
FIG. 10 shows PET-MRI imaging with administration of [$^{11}$C]CN133 of FIG. 3 with SAHA infusion (5 mg/kg) started at 45 minutes post first administration of the [$^{11}$C]CN133 until the end of second scan. The time-activity curves showed the significant blocking with SAHA infusion in the organs. A: baboon heart wall; B: baboon spleen; C: baboon kidney; and D: baboon pancreas.

FIG. 10 shows [11C]CN133 PET-MRI imaging with baboon. SAHA infusion (5 mg/kg) started at 45 minutes post first [11C]CN133 administration until the end of second scan. The time-activity curves showed the significant blocking with SAHA infusion in the organs. A: heart wall; B: spleen; C: kidney; and D, pancreas. Thus, the peripheral signal from CN133 can be blocked by SAHA (proof of HDAC engagement in peripheral organs).

In Vivo PET-MR Imaging with [$^{11}$C]CN133 in Human

Figure 14:
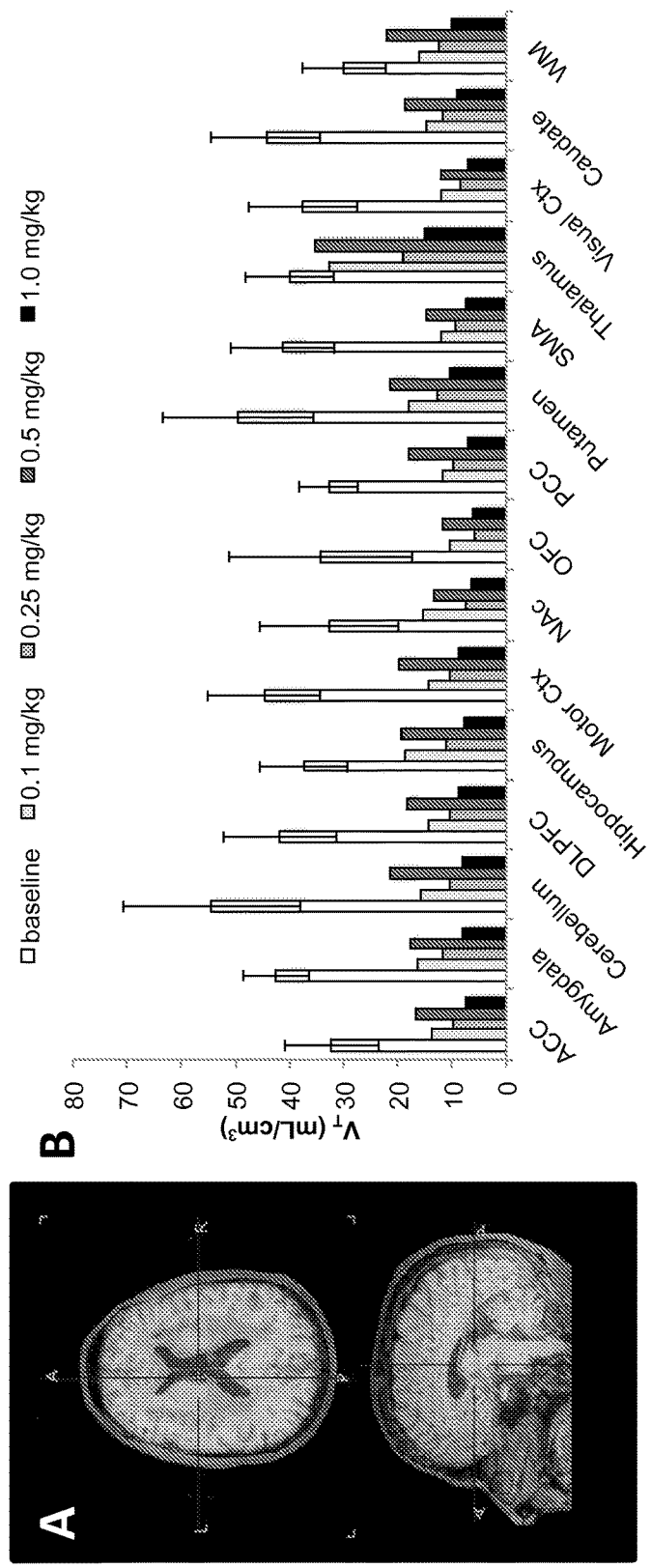
FIG. 14A shows uptake of the radiotracer [$^{11}$C]CN133 in human brain where differential levels of radiotracer uptake (color scale range; red=high uptake, blue=low uptake) are indicative of HDAC expression/binding availability throughout the brain. Summed images (40-90 min) reveal differential uptake throughout the brain.
FIG. 14B shows quantification of total distribution volume ($V_t$) in specific regions of the non-human primate brain, where pretreatment with non-radioactive CN133 blocked uptake of the radiotracer in a dose- and region-specific way, again, indicative of differences in HDAC target expression/binding availability. Dose responsive blockade of radiotracer binding provides evidence of specific binding signal. The graph legends left to right correspond left to right in the groups of bars in the graph.

Following FDA-approval of [$^{11}$C]CN133 for imaging use in healthy human subjects, we successfully imaged dynamic uptake of the radiotracer in human brain (see FIG. 14A). Mean uptake of the probe was averaged over scan timepoints 40 min-90 min and revealed differential uptake throughout the human brain, indicative of differential HDAC target density. Regional analysis was achieved in a non-human primate dataset (see FIG. 14B) and the same software tools provide that quantification of radiotracer binding can be accomplished on human [$^{11}$C]CN133 PET datasets.

Discussion

Increasing evidence points to an important role for histone deacetylases in diseases, including, but not limited to, brain disorders, heart disease and cancers, but there is no prior method to measure the histone deacetylase expression in human with such diseases and monitor the disease progress and evaluate the therapeutics. Non-invasive PET imaging provides a tool for the detection and quantification of histone deacetylase expression in vivo. To date, however, there is still no validated PET radiotracer available for histone deacetylase imaging, particularly in the brain. Development of CNS-penetrant and specific PET radiotracers for histone deacetylase and any epigenetic processes is challenging. There are a number of major factors that determine the success of a CNS-penetrant radiotracer candidate: (a) BBB penetration. Small molecular weight (<400 Daltons) and a high degree of lipophilicity are required for a tracer to pass the BBB which is composed of a lipid bilayer; (b) A radiotracer should have high specific binding (and low nonspecific binding), which is challenging to predict. This would be visualized as binding of an unlabeled form of the radiotracer would saturate the HDACs in the brain resulting in decreased binding of radiotracer to its target. Likewise, unlabeled compound binding would also be expected to alter the distribution and pharmacokinetics the radioligand in the brain; (c) Binding affinity. The binding affinity of a radiotracer for the target must be high enough to produce sufficient signal for detection; (d) Metabolites. A tracer candidate can still be rendered unusable in vivo if it is metabolized rapidly and those metabolites pervade regions of interest.

We have designed, synthesized and identified [$^{11}$C] CN133 as a molecule ready for translation to human HDAC-PET imaging. CN133 is a hydroxamic acid based HDAC inhibitor with an adamantyl group. One reason to choose hydroxamic acid is its fast-on binding towards HDAC enzymes, allowing the PET detection with short half-life isotopes, such as carbon-11. Most of small molecules have limited brain penetration due to the presence of BBB, to avoid this problem, we added an adamantyl group, as a BBB carrier, into the structure. The measured Log D of CN133 is at 2.03, indicating the good BBB penetration which is consistent with our imaging results. CN133 is very potent HDAC inhibitor compared with SAHA, exhibiting sub-nanomolar binding towards HDAC1, HDAC 2, HDAC 3 and HDAC 6 in vitro.

We tested PET imaging with [$^{11}$C]CN133 in rats and baboons as a model before we evaluated it in humans. After injection of [$^{11}$C]CN133 in the baboon, radioactivity reached its peak at about 1 minute in the brain after injection. As we expected, the in vivo distribution studies with [$^{11}$C] CN133 demonstrated high uptake of radioactivity in the regions of the brain. Blocking studies that were conducted in rats showed dose-dependent blocking manner in rats brain (FIG. 5B), suggesting that this radiotracer will be a valuable tool for determination of HDAC expression and occupancy and for studying regional HDAC enzymes in the brain. To exclude the interaction between CN133 and P-glycoprotein, the CsA pre-treat study was conducted and we did not observe any different between the treated and vehicle animals (see FIG. 6A). To test the saturable binding with unlabeled CN133 and other HDAC inhibitors, we chose SAHA, which is a pan-HDAC inhibitor with limited brain permeability and CN54, which is a brain-penetrant HDAC inhibitor. Both inhibitors showed blocking in peripheral in rats, but SAHA did not block the brain uptake as expected. In baboons, CN133 showed blockade in the brain and peripheral organs, the successful blocking of the accumulation of [$^{11}$C]CN133 radioactivity in rats and baboons with unlabeled CN133 demonstrated that the binding of the radiotracer is specific in the brain and peripheral organs. Also, binding assays indicated that CN133 at 100 times its HDAC $IC_{50}$ has minimal (if any) off target binding. These results indicated that [$^{11}$C]CN133 would be used for evaluate the pharmacological properties of histone deacetylase inhibitors.

In summary, [$^{11}$C]CN133 has been developed as a histone deacetylase PET imaging agent that readily penetrates the blood-brain barrier and binds to HDAC subtypes (such as HDAC1, HDAC 2, HDAC 3 and HDAC 6) in the brain and exhibited properties for quantitative imaging of HDAC in the brain and in peripheral organs in vivo. The non-invasiveness of histone deacetylase PET imaging allows repeated measurements over the life span of animals, providing an ideal tool for monitoring progression of HDAC expressions. [$^{11}$C]CN133 can be used as a PET radioligand for studying histone deacetylases in disorders when altered regulation of the histone deacetylases is found. The approach is also valuable for evaluation of potential drugs in vivo, therapy response can be compared in the same animal before drug treatment.

Relationships between protein density changes for the "epigenetic machinery" and disease are now established. However to date there is not a single, validated radiotracer for visualizing any component of the epigenetic machinery in humans. We have described herein a highly brain penetrant PET imaging agent to visualize histone deacetylase enzymes that we have validated for CNS imaging using rodent and non-human primate animal models. These data demonstrate that our imaging agents, including the non-limiting examples shown and described herein such as [$^{11}$C]CN133 shown in FIG. 3, can provide the first associations of class-I HDAC density with brain function and dysfunction. We integrated non-human primate imaging as part of our initial experiments given the physiological and anatomical similarities between baboon and human. Compounds of the invention have unique BBB penetrance and kinetics, for example, [$^{11}$C]CN133 shown in FIG. 3 exhibits dose-dependent specific binding in rodents and non-human primates. Further, [$^{11}$C]CN133 shown in FIG. 3 has sub-nanomolar potency for certain HDAC isoforms, and CN133 binding can be modeled to determine distribution volume from a single injection. CN133 shows sub-nanomolar efficacy in cell cultures. While we used the CNS as our initial target for imaging, [$^{11}$C]CN133 shown in FIG. 3 exhibits high uptake and specific binding indicative of HDAC engagement in peripheral organs. Compounds of the invention could be imaging agents useful for studying HDAC in CNS disorders, cardiac disease, cancer, and diseases of other major organ systems. [$^{11}$C]CN133 has great properties as a radiotracer and the data we have presented indicate that CN133 (the non-radioactive analog) may be an excellent tool molecule for HDAC inhibition in animals models and perhaps even a molecule with therapeutic potential. Compounds of the invention are envisioned as imaging agents useful in determining HDAC changes in disease. CN133 could be a drug molecule applicable as a therapy in disease. CN133 could be a tool compound for biological studies.

Although the present invention has been described in detail with reference to certain embodiments, one skilled in the art will appreciate that the present invention can be practiced by other than the described embodiments, which have been presented for purposes of illustration and not of limitation. Therefore, the scope of the appended claims should not be limited to the embodiments contained herein.

What is claimed is:

1. A compound of formula (I):

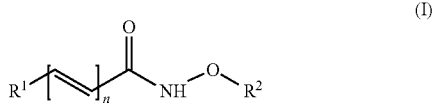

(I)

wherein R$^1$ is a moiety including a substituted or unsubstituted adamantyl group and a contrast agent,
wherein R$^2$ represents hydrogen, or substituted or unsubstituted alkyl, or substituted or unsubstituted aryl, substituted or unsubstituted heteroaryl, or substituted or unsubstituted heterocyclic, and
wherein n is an integer selected from 0 or 1, and
wherein the compound has a brain to plasma ratio greater than 1, and wherein at least one atom in R$^1$ is replaced with a positron emitter selected from the group consisting of $^{11}$C, $^{13}$N, $^{15}$O, $^{18}$F, $^{34m}$Cl, $^{38}$K, $^{45}$Ti, $^{51}$Mn, $^{52m}$Mn, $^{52}$Fe, $^{55}$Co, $^{60}$Cu, $^{61}$Cu, $^{62}$Cu, $^{64}$Cu, $^{66}$Ga, $^{68}$Ga, $^{71}$As, $^{72}$As, $^{74}$As, $^{75}$Br, $^{76}$Br, $^{82}$Rb, $^{86}$Y, $^{89}$Zr, $^{90}$Nb, $^{94m}$Tc, $^{110m}$In, $^{118}$Sb, $^{120}$I, $^{121}$I, $^{122}$I, and $^{124}$I.

2. The compound of claim 1 wherein:
the positron emitter is $^{11}$C or $^{18}$F.

3. The compound of claim 1 wherein:
the contrast agent is a photon emitter.

4. The compound of claim 3 wherein:
the photon emitter is selected from the group consisting of $^{67}$Ga, $^{99m}$Tc, $^{111}$In, $^{123}$I, $^{125}$I, $^{131}$I, and $^{201}$Tl.

5. The compound of claim 1 wherein:
the contrast agent is a contrast agent for magnetic resonance imaging.

6. The compound of claim 5 wherein:
the magnetic resonance imaging contrast agent is selected from the group consisting of ions of gadolinium, manganese, and iron.

7. The compound of claim 1 wherein:
the compound has an octanol-water partition coefficient (log D) in the range of 1 to 3.

8. The compound of claim 1 wherein:
n is 1.

9. A method for in vivo imaging of a subject, the method comprising:
(a) administering to the subject the compound of claim 1;
(b) waiting a time sufficient to allow the compound to accumulate at a tissue or cell site to be imaged; and
(c) imaging the cells or tissues with a non-invasive imaging technique.

10. The method of claim 9 wherein:
the non-invasive imaging technique is selected from positron emission tomography imaging, positron emission tomography with computed tomography imaging, or positron emission tomography with magnetic resonance imaging.

11. A method for detecting histone deacetylase in a subject, the method comprising:
(a) administering to the subject the compound of claim 1;
(b) waiting a time sufficient to allow the compound to accumulate at a tissue or cell site in a brain of the subject to be imaged; and
(c) imaging the cells or tissues with a non-invasive imaging technique.

* * * * *

UNITED STATES PATENT AND TRADEMARK OFFICE
CERTIFICATE OF CORRECTION

PATENT NO. : 10,188,756 B2
APPLICATION NO. : 15/030214
DATED : January 29, 2019
INVENTOR(S) : Jacob M. Hooker et al.

Page 1 of 1

It is certified that error appears in the above-identified patent and that said Letters Patent is hereby corrected as shown below:

In the Specification

Column 12, Line 45, "$^{124}$I, is" should be --$^{124}$I. Preferably, the positron emitter is--.

Column 30, Line 50, "$^{11}CH_4$" should be --$^{11}CO_2$--.

Signed and Sealed this
Second Day of April, 2019

Andrei Iancu
*Director of the United States Patent and Trademark Office*